US010281709B2

(12) United States Patent
Root et al.

(10) Patent No.: US 10,281,709 B2
(45) Date of Patent: May 7, 2019

(54) HANDHELD MOBILE LIGHT SOURCE

(71) Applicant: Acera LLC, Beverly, MA (US)

(72) Inventors: Thomas V. Root, Beverly, MA (US);
Michael Cook, Marblehead, MA (US);
Thomas Davis, Hollis, NH (US);
Michael S. Epstein, Annapolis, MA (US); Carlton Jones, Boxford, MA (US); David Leo, Winchester, MA (US)

(73) Assignee: Acera, LLC, Beverly, MA (US)

( * ) Notice: Subject to any disclaimer, the term of this patent is extended or adjusted under 35 U.S.C. 154(b) by 182 days.

(21) Appl. No.: 15/338,138

(22) Filed: Oct. 28, 2016

(65) Prior Publication Data
US 2017/0123131 A1 May 4, 2017

Related U.S. Application Data

(60) Provisional application No. 62/247,456, filed on Oct. 28, 2015, provisional application No. 62/247,454,
(Continued)

(51) Int. Cl.
*A61B 1/00* (2006.01)
*A61B 1/06* (2006.01)
(Continued)

(52) U.S. Cl.
CPC ........ *G02B 23/2453* (2013.01); *A61B 1/0011* (2013.01); *A61B 1/00126* (2013.01);
(Continued)

(58) Field of Classification Search
CPC ............ G02B 23/2453; G02B 23/2469; G02B 1/041; G02B 6/0006; G02B 6/0008;
(Continued)

(56) References Cited

U.S. PATENT DOCUMENTS 2,908,197 A 10/1959 Wells
3,285,242 A * 11/1966 Wallace ................. F21L 14/00
362/105
(Continued)

FOREIGN PATENT DOCUMENTS

EP 2846179 A2 3/2015
WO 2008016895 A2 2/2008

OTHER PUBLICATIONS

Chen, G., CN 205079073, Sep. 3, 2016, English Abstract (Year: 2016).*
(Continued)

*Primary Examiner* — Mary Ellen Bowman
(74) *Attorney, Agent, or Firm* — Nelson Mullins Riley & Scarborough LLP; Reza Mollaaghababa; Ashley T. Brzezinski

(57) ABSTRACT

In one aspect, a handheld lighting system is disclosed, which comprises a handheld housing extending from a proximal end to a distal end, and a light module disposed at least partially in the housing. The handheld lighting system further includes a removable and replaceable power module that is coupled to the housing (e.g., it is at least partially disposed within the housing) and is electrically coupled to the light module, e.g., through a pair of electrical leads, for providing electrical power thereto. Light intensity from the light module may be controlled from a knob on the power module. Various adapters can allow the lighting system to attach to a multitude of medical, industrial, dental or veterinary endoscopes or other instruments.

46 Claims, 23 Drawing Sheets

Related U.S. Application Data filed on Oct. 28, 2015, provisional application No. 62/247,451, filed on Oct. 28, 2015.

(51) Int. Cl.

| | |
|---|---|
| *A61B 1/07* | (2006.01) |
| *F21L 4/00* | (2006.01) |
| *F21V 3/00* | (2015.01) |
| *F21V 5/04* | (2006.01) |
| *F21V 8/00* | (2006.01) |
| *G02B 1/04* | (2006.01) |
| *G02B 6/38* | (2006.01) |
| *G02B 6/42* | (2006.01) |
| *F21L 14/02* | (2006.01) |
| *F21V 15/01* | (2006.01) |
| *F21V 17/12* | (2006.01) |
| *F21V 23/04* | (2006.01) |
| *F21V 23/06* | (2006.01) |
| *F21V 29/77* | (2015.01) |
| *F21V 29/89* | (2015.01) |
| *G02B 19/00* | (2006.01) |
| *G02B 23/24* | (2006.01) |
| *H05B 33/08* | (2006.01) |
| *F21Y 115/10* | (2016.01) |
| *F21W 131/20* | (2006.01) |
| *F21W 131/40* | (2006.01) |

(52) U.S. Cl.
CPC ............ *A61B 1/0669* (2013.01); *F21L 4/005* (2013.01); *F21V 3/00* (2013.01); *F21V 5/04* (2013.01); *F21V 5/048* (2013.01); *F21V 15/01* (2013.01); *F21V 17/12* (2013.01); *F21V 23/0414* (2013.01); *F21V 23/06* (2013.01); *F21V 29/773* (2015.01); *F21V 29/89* (2015.01); *G02B 1/041* (2013.01); *G02B 6/0006* (2013.01); *G02B 6/0008* (2013.01); *G02B 6/4206* (2013.01); *G02B 6/428* (2013.01); *G02B 6/4231* (2013.01); *G02B 6/4269* (2013.01); *G02B 19/0066* (2013.01); *G02B 23/2469* (2013.01); *H05B 33/0845* (2013.01); *A61B 1/00105* (2013.01); *A61B 1/07* (2013.01); *F21L 4/00* (2013.01); *F21L 14/02* (2013.01); *F21W 2131/20* (2013.01); *F21W 2131/40* (2013.01); *F21Y 2115/10* (2016.08); *G02B 6/3807* (2013.01)

(58) Field of Classification Search
CPC .. G02B 6/4206; G02B 6/4231; G02B 6/4269; G02B 6/428; G02B 19/0066; F21V 29/773; F21V 29/89; F21V 3/00; F21V 5/04; F21V 5/048; F21V 15/01; F21V 17/12; F21V 23/0414; F21V 23/06; A61B 1/0011; A61B 1/00126; A61B 1/0669; F21L 4/005; H05B 33/0845
See application file for complete search history.

(56) References Cited

U.S. PATENT DOCUMENTS

| | | | | |
|---|---|---|---|---|
| 3,592,199 | A | * | 7/1971 | Ostensen ................ A61B 1/267 362/197 |
| D331,634 | S | | 12/1992 | Browne |
| 5,353,208 | A | * | 10/1994 | Moore ..................... F21L 4/005 362/202 |
| 5,743,848 | A | * | 4/1998 | Koeda ....................... A61B 1/07 600/160 |
| 6,007,485 | A | * | 12/1999 | Koeda ................. A61B 1/00126 600/178 |
| 6,099,147 | A | * | 8/2000 | Ziegenfuss ............. F21L 4/045 362/158 |
| 6,135,947 | A | * | 10/2000 | Watanabe ........... A61B 1/00117 600/160 |
| 6,257,741 | B1 | * | 7/2001 | Williams ............... A61B 1/0669 362/296.01 |
| 6,819,505 | B1 | | 11/2004 | Cassarly et al. |
| 6,937,791 | B2 | | 8/2005 | Guy |
| 6,991,603 | B2 | | 1/2006 | Krupa et al. |
| D533,939 | S | | 12/2006 | Root et al. |
| 7,193,519 | B2 | | 3/2007 | Root et al. |
| 7,198,397 | B2 | | 4/2007 | Bennett et al. |
| 7,229,201 | B2 | | 6/2007 | Krupa et al. |
| D551,762 | S | | 9/2007 | Root et al. |
| D561,336 | S | | 2/2008 | Laflash et al. |
| D581,052 | S | | 11/2008 | Root et al. |
| D623,786 | S | | 9/2010 | Wessel |
| 7,798,692 | B2 | | 9/2010 | Krupa et al. |
| D629,537 | S | | 12/2010 | Hsu et al. |
| D631,567 | S | | 1/2011 | Lodhie |
| 8,033,704 | B2 | | 10/2011 | Krupa et al. |
| 8,152,715 | B2 | | 4/2012 | Root et al. |
| D662,231 | S | | 6/2012 | Sakamoto et al. |
| D663,445 | S | | 7/2012 | Sakamoto et al. |
| D663,464 | S | | 7/2012 | Lee |
| D666,340 | S | | 8/2012 | Sakamoto et al. |
| D669,200 | S | | 10/2012 | Chen et al. |
| D671,241 | S | | 11/2012 | Sakamoto et al. |
| D671,242 | S | | 11/2012 | Sakamoto et al. |
| D671,243 | S | | 11/2012 | Sakamoto et al. |
| D675,349 | S | | 1/2013 | Parker et al. |
| D715,463 | S | | 6/2013 | Xue |
| D685,506 | S | | 7/2013 | Pickard et al. |
| D690,383 | S | | 9/2013 | Sheikh et al. |
| 9,022,628 | B2 | | 5/2015 | Krupa et al. |
| 9,055,863 | B2 | | 6/2015 | Krupa et al. |
| D739,586 | S | | 9/2015 | Hong |
| D744,674 | S | | 12/2015 | Wu et al. |
| D753,322 | S | | 4/2016 | Taylor |
| D760,928 | S | | 7/2016 | Bao |
| D768,321 | S | | 10/2016 | Inskeep |
| D775,752 | S | | 1/2017 | Nook et al. |
| D778,473 | S | | 2/2017 | Cooper |
| D793,595 | S | | 8/2017 | Lesperance et al. |
| D804,064 | S | | 11/2017 | Taylor et al. |
| D810,325 | S | | 2/2018 | Guo |
| D813,424 | S | | 3/2018 | Shum et al. |
| 2004/0246744 | A1 | | 12/2004 | Krupa et al. |
| 2005/0162848 | A1 | * | 7/2005 | Dalton .................... F21L 4/085 362/157 |
| 2005/0201100 | A1 | | 9/2005 | Cassarly et al. |
| 2007/0253188 | A1 | | 11/2007 | Klipstein |
| 2008/0174996 | A1 | | 7/2008 | Lu et al. |
| 2009/0185392 | A1 | | 7/2009 | Krupa et al. |
| 2010/0226127 | A1 | | 9/2010 | Bigliatti et al. |
| 2010/0277894 | A1 | * | 11/2010 | Kim ........................ F21L 4/00 362/105 |
| 2011/0194295 | A1 | | 8/2011 | Householder |
| 2015/0219313 | A1 | | 8/2015 | Marcaly |
| 2017/0122525 | A1 | | 5/2017 | Root et al. |
| 2017/0123199 | A1 | | 5/2017 | Jones et al. |

OTHER PUBLICATIONS

Invitation to Pay Additional Fees and, Where Applicable, Protest Fee for corresponding PCT/US2016/059451, dated Mar. 16, 2017; 6 pages.

International Search Report/Written Opinion for corresponding PCT/US2016/059451, dated Jun. 19, 2017; 15 pages.

International Search Report/Written Opinion for corresponding PCT Application No. PCT/US2016/059406, dated Apr. 7, 2017, 11 pages.

Invitation to Pay Additional Fees for corresponding PCT Application No. PCT/US2016/059361, dated Feb. 3, 2017, 6 pages.

(56) References Cited

OTHER PUBLICATIONS

International Search Report/Written Opinion for corresponding PCT Application No. PCT/US2016/059361, dated Apr. 4, 2017, 16 pages.
International Preliminary Report on Patentability for corresponding PCT Application No. PCT/US2016/059361, dated May 11, 2018, 10 pages.

* cited by examiner

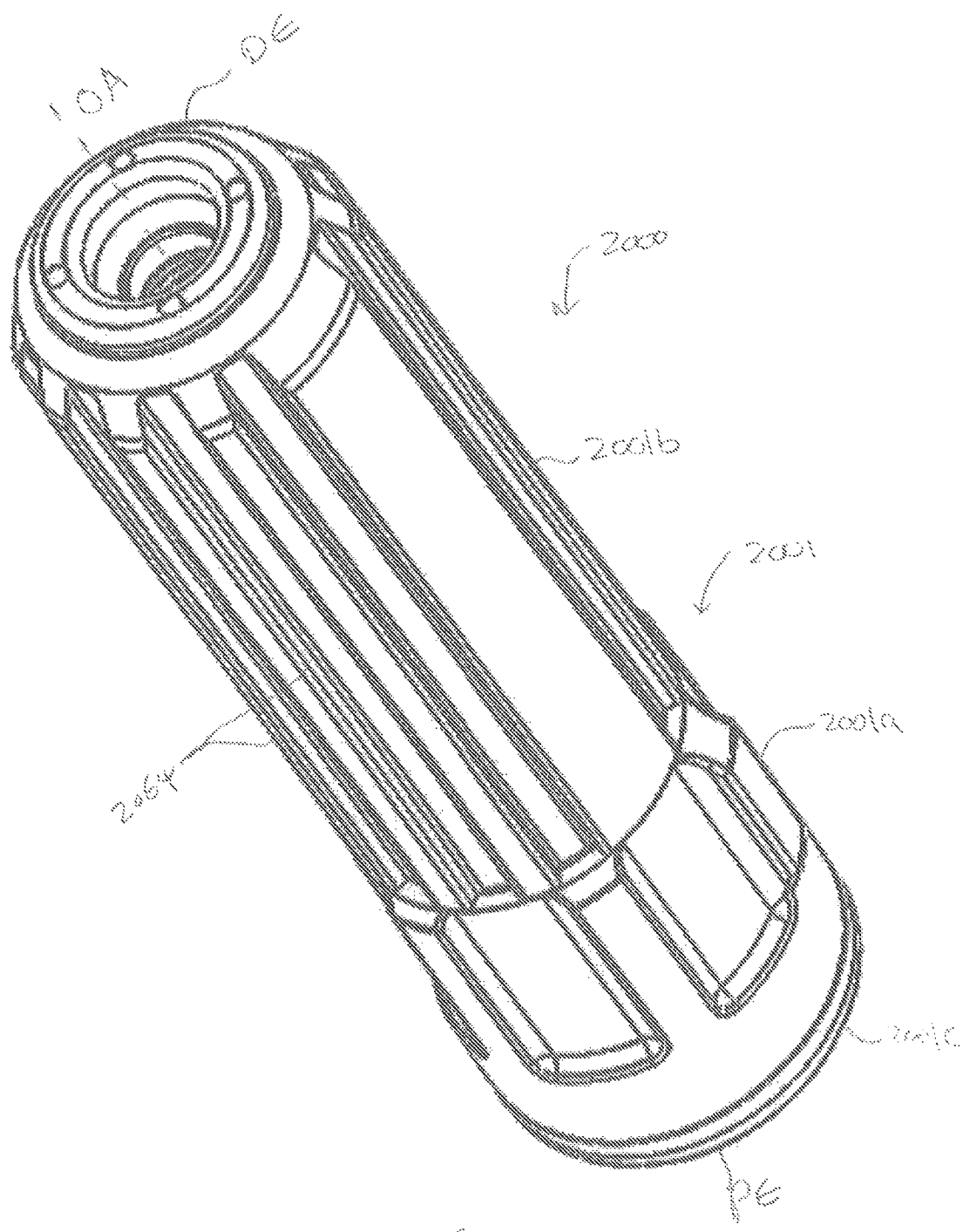

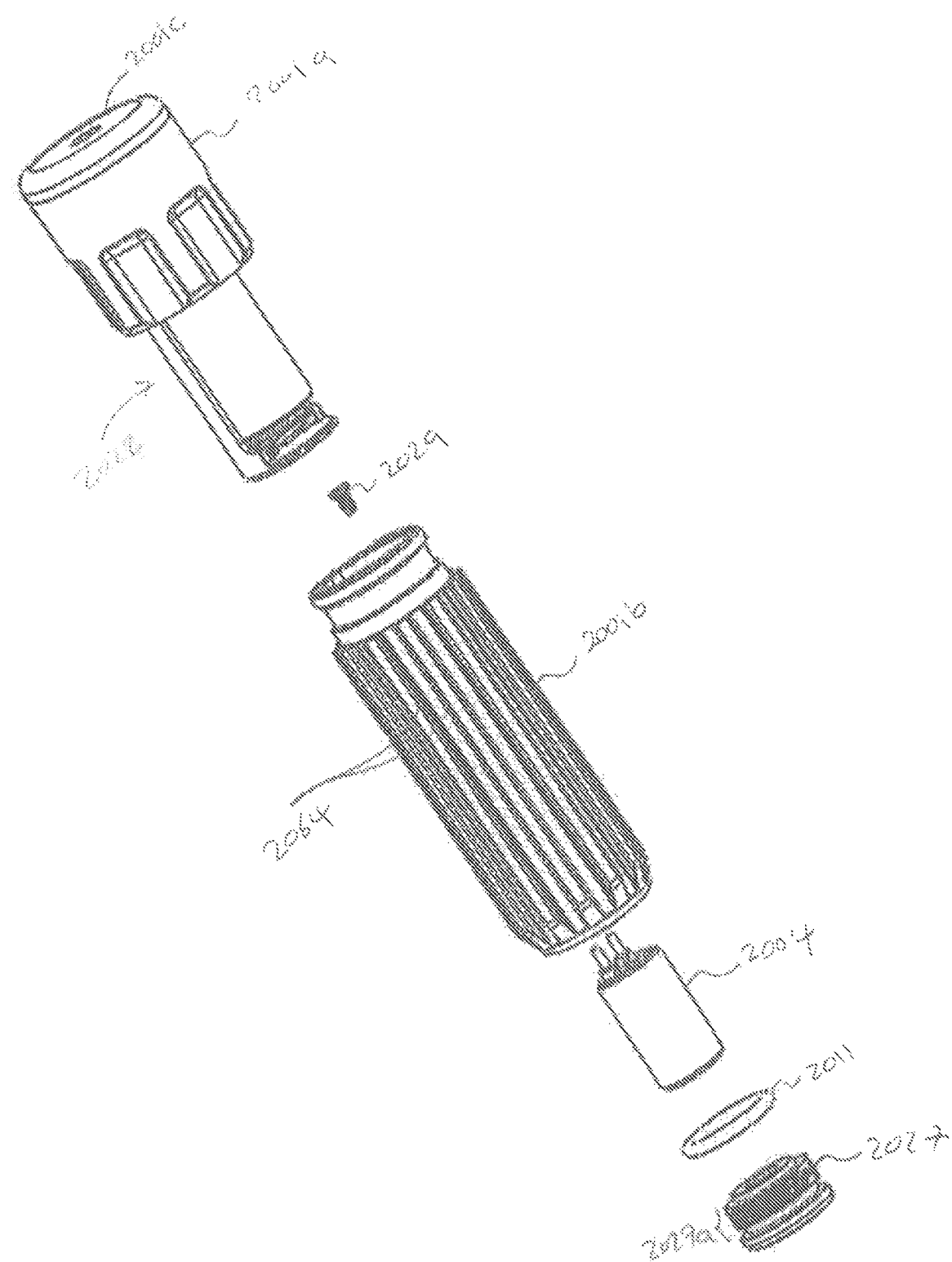

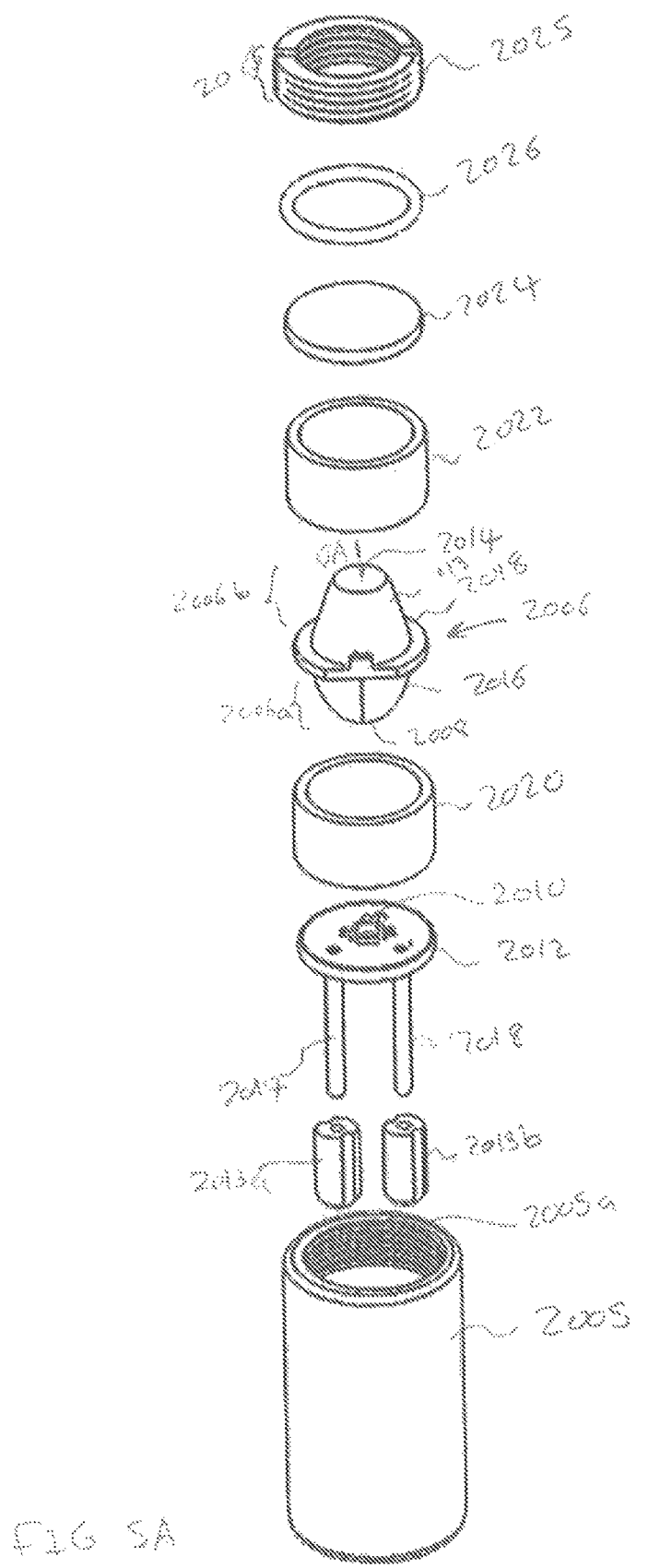

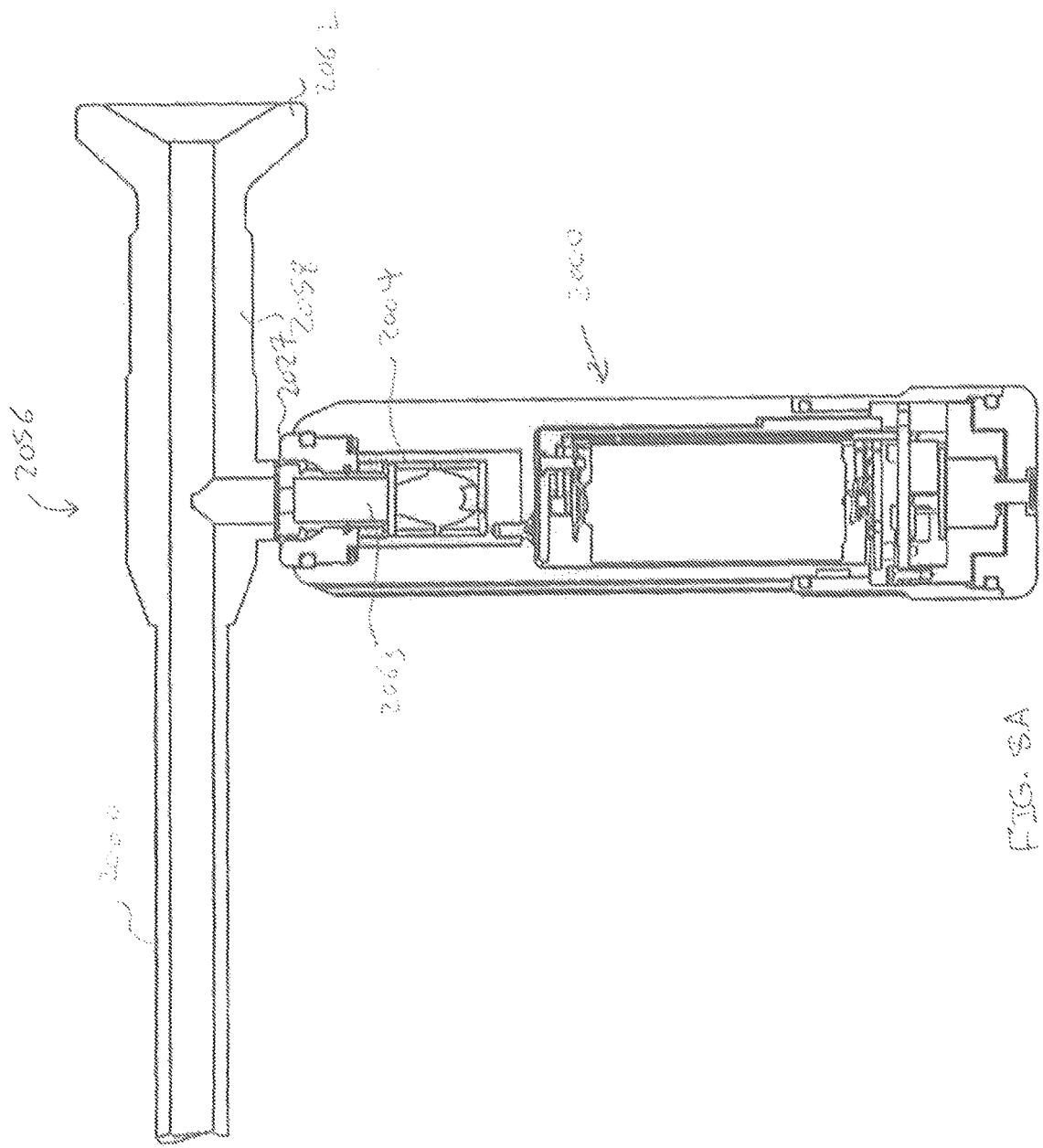

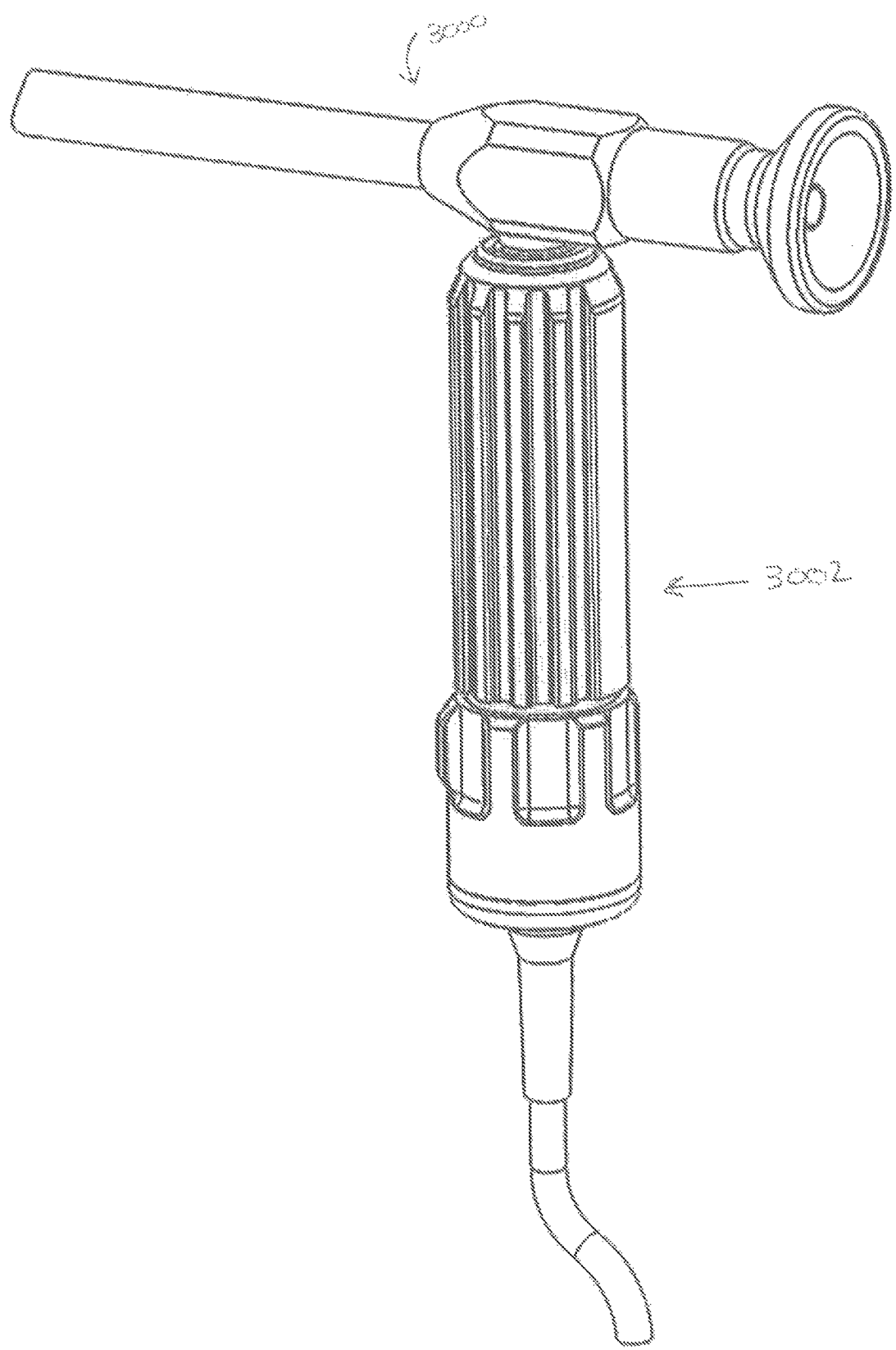

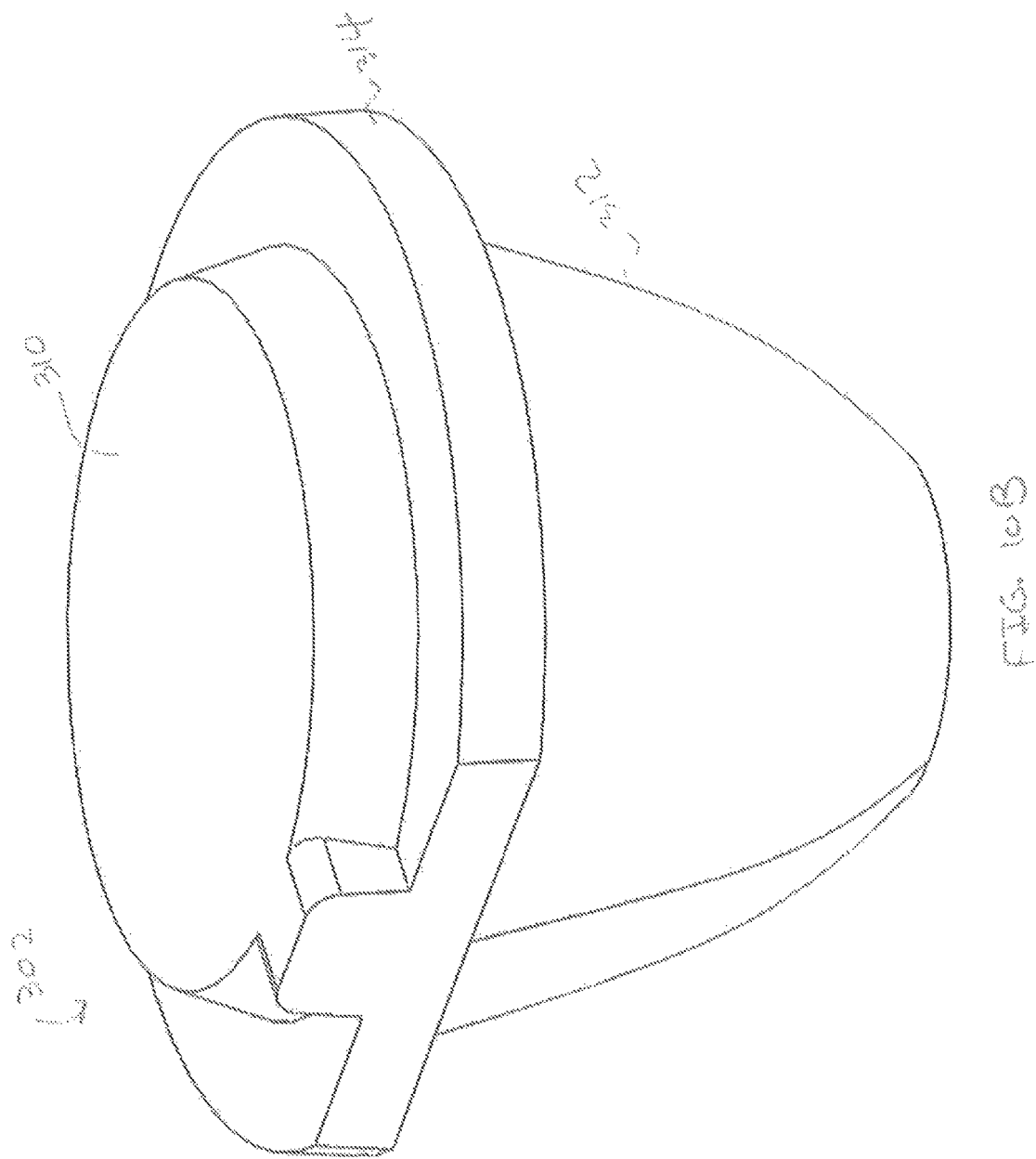

HANDHELD MOBILE LIGHT SOURCE

RELATED APPLICATIONS

The present application claims priority to a provisional patent application entitled "Handheld mobile light source" having an application No. 62/247,456 filed on Oct. 28, 2015, and a provisional patent application entitled "Embeddable module for high output LED" having an application No. 62/247,454 filed on Oct. 28, 2015, and a provisional patent application entitled "Elliptical optical lens for high output LED" having an application No. 62/247,451 filed on Oct. 28, 2015, each of which is herein incorporated by reference in its entirety.

The present application is also related to utility applications entitled "Embeddable module for high output LED" and "Elliptical optical lens for high output LED," which are being filed concurrently herewith and are hereby incorporated by reference in their entirety.

BACKGROUND

The present invention relates generally to a handheld lighting system that can be mechanically coupled to a variety of devices, such as medical and industrial endoscopes, to provide high intensity, low heat light.

Many devices that operate in small, closed areas, require a light source to operate. For example, laparoscopic and endoscopic procedures are conducted through small incisions in the skin or natural body orifices. In order to operate or view an internal area, medical professionals use endoscopes that have small, elongated distal portions that fit within these small openings but are long enough to reach the internal areas within the body. These instruments need to provide precise and accurate movement in order to reach areas within the body that are difficult to access. The distal working ends of the endoscopes usually contain a small camera that allows a medical professional to view an internal area within the body during the procedure. The camera and the working end of the endoscope must have adequate remotely controlled illumination to permit the medical professional to view the internal area. In some endoscopes, a camera positioned outside the patient's body can receive, via a light guide, radiation reflected from an illuminated internal area and form an image of that area for viewing by a medical professional.

Many conventional light sources are inefficient in converting electrical power to light, and must be connected to external power sources, limiting their range of motion. Light emitting diodes (LED) can produce light without generating a large amount a heat, but they are not typically capable of generating enough illumination to be useful in a variety of applications, such as endoscopic systems. Even if multiple LEDs are employed, in many conventional systems, the inefficient coupling of the light generated by the LEDs into a light guide of a device can result in insufficient intensity.

Accordingly, there is a need for enhanced lighting systems, and particularly a need for such systems that can be employed to provide light to a variety of medical and industrial devices.

SUMMARY

In one aspect, a handheld lighting system is disclosed, which comprises a handheld housing extending from a proximal end to a distal end, and a removable and replaceable light module disposed at least partially in the housing. The handheld lighting system further includes a power module that is coupled to the housing (e.g., it is at least partially disposed within the housing) and is electrically coupled to the light module, e.g., through a pair of electrical leads, for providing electrical power thereto.

The light module further includes an adapter disposed at the distal end of the housing for coupling the lighting system to a device having one or more light guides, e.g., one or more optical fibers, for providing light from the light module to those light guide(s), which can in turn transfer the light to a field of view for illumination thereof. In some embodiments, the adapter is removable and replaceable.

In some embodiments, the handheld housing includes at least a portion formed of a thermally conductive material, e.g., a metal such as aluminum. In some such embodiments, the thermally conductive portion includes a corrugated external surface for facilitating transfer of heat generated by the light module and/or the power module to an external environment. In some such embodiments, the corrugated external surface includes a plurality of fins that increase its surface area, thereby enhancing heat dissipation through that surface. In some such embodiments, the fins extend longitudinally and have a height in a range of about ⅛ inches to about ⅙ inches.

In some embodiments, the power module allows adjusting the intensity of the light generated by the light module. In some embodiments, the light module includes a pair of electrical connectors (leads) protruding through an internal wall of the housing for electrically connecting the light module to the power module.

In some embodiments, the housing includes a first enclosure extending from the distal end of the housing to an internal wall thereof for receiving the light module, and a second housing extending from the internal wall to a proximal end of the housing for receiving the power module.

In some embodiments, the housing includes a rotatable shell coupled to the power module such that the rotation of the rotatable shell adjusts the power supplied by the power module to the light module, thereby changing the intensity of the light generated by the light module. In some such embodiments, the housing includes a heat sink portion to which the rotatable shell is coupled. By way of example, the rotatable shell can include a spring-loaded ball that can engage within a retaining groove provided in an inner wall of the heat sink portion. By way of example, the power module can include an adjustable potentiometer electrically coupled to a light source of the light module and mechanically coupled to said rotatable shell such that a rotation of the shell results in a change of resistance of the potentiometer, thereby adjusting the intensity of the light generated by the light module.

In some embodiments, the light module includes a hollow chamber extending from a proximal end to a distal end, a lens positioned removably and replaceably in the hollow chamber, the lens having a lens body comprising an input surface for receiving light from the light source (e.g., an LED) and an output surface through which light exits the lens, said lens further comprising a collar encircling at least partially said lens body.

The light module can further include at least one sleeve disposed in the hollow chamber in contact with the lens collar for providing mechanical support to the lens, and an optical window disposed in the hollow chamber and optically coupled to said output surface of the lens such that the light exiting the lens passes through the optical window before exiting the light module. The light source can be coupled to the hollow chamber at a proximal end thereof for providing light to said input surface of the lens. The optical window can be formed of any suitable material, such as sapphire, quartz, glass, etc.

In some embodiments of the above light module, a retaining window can be coupled releasably to the distal end of the hollow chamber, e.g., via a plurality of threads engaging with respective threads at the distal end of the hollow chamber. The retaining window can have an opening for coupling to an adapter, which can in turn couple to a light guide so as to deliver the light from the light module to the light guide.

In some embodiments, a gasket can be disposed between the optical window and the retaining window.

The light module can further include a printed circuit (PC) board on which the light source is mounted. The PC board can include a plurality of electrical leads for applying electrical power to the light source and optionally controlling its operation.

A plate can be coupled to the distal end of the light module's housing, where the plate can have a plurality of openings through which the electrical leads of the light module can extend for coupling to the power module of the lighting system.

In some embodiments, the light module can include a shoulder for holding the lens within its housing. For example, the light module can include at least one sleeve supporting the lens above the PC board. In some embodiments, a pair of sleeves are disposed on opposite sides of the lens collar, where one sleeve supports the lens above the PC board and the other sleeve supports the optical window above the lens.

A plurality of different lenses can be employed in the light module. By way of example, the lens can include a lens body comprising a proximal section having said input surface and a distal section having said output surface. The proximal section can include a substantially elliptical peripheral surface receiving at least a portion of the light entering the lens body via said input surface and directing at least some of said received light via total internal reflection to said distal section such that at least a portion of the light directed to the distal section exits the lens body through said output surface. The peripheral elliptical surface is characterized by a proximal focal point and a distal focal point. In some embodiments, the peripheral surface is shaped such that the distal focal point is positioned external to the lens body, e.g. at a distance above the output surface of the lens. In other embodiments, the distal focal point can be positioned in the lens body, e.g., below the output surface or at the output surface. Further, in some embodiments, the proximal focal point is positioned substantially at or in proximity of the light source such that the elliptical surface transfers at least a portion of the light emitted by the light source from the proximal focal point to the distal focal point. In many embodiments, the focal points are disposed on an optical axis of the lens, e.g., an axis about which the lens body is rotationally symmetric.

In some embodiments, the input surface includes a central convex portion and a peripheral portion surrounding said convex portion. In such embodiments, the input surface can form a surface of a cavity configured to receive at least partially the light source. In some such embodiments, the proximal focal point can be positioned in the input cavity.

In some embodiments, the peripheral portion of the input surface can include a proximal concave segment and a distal convex segment.

In some embodiments, the peripheral portion of the input surface is shaped such that at least a portion of the light entering the lens body via said peripheral portion propagates to said peripheral elliptical surface to be reflected thereby. The peripheral portion of the input surface can be shaped such that at least about 80%, or at least about 90%, or at least about 95% (and preferably 100%) of the light entering the lens body via the peripheral portion propagates to the peripheral surface of the lens body to be reflected thereby.

In some embodiments, the convex portion of the input surface can exhibit a positive optical power in a range of about 50 D to about 300 D. In some such embodiments, at least a portion of the light entering the lens body via said convex portion propagates to the output surface without striking the peripheral surface.

In some embodiments, the input surface of the lens is configured to capture at least about 70%, or at least about 80%, or at least about 90%, or at least about 95% (and preferably 100%) of the light energy emitted by the light source. In some embodiments, the lens transfers the light energy emitted by the light source from the light source to its output surface with an efficiency of at least about 70%, or at least about 80%, or at least about 90% or at least about 95%.

In some embodiments, the light module of the lighting system couples the light emitted by the light source to a light guide of a device to which the lighting system is coupled with an efficiency of at least about 30%, or at least about 40%, or at least about 50%, or at least about 60%, or at least about 70%, or at least about 80%, or at least about 90%.

In some embodiments, the output surface of the lens is substantially flat and is orthogonal to an optical axis of the lens.

The lens can be formed of a variety of different materials, such as polymeric materials, or glass. Some examples of suitable materials include, without limitation, polymethymethacylate (PMMA), polycarbonate, and silicone.

In some embodiments, the power module of the lighting system can be battery operated, and in other embodiments, the power module can receive AC line voltage and convert that voltage to a DC voltage suitable for application to the light source.

In some embodiments, the handheld lighting system can include a light module, which includes a housing providing a hollow chamber extending from a proximal end to a distal end, a lens positioned in said hollow chamber, said lens having a lens body comprising an input surface for receiving light from a light source and an output surface through which light exits the lens body, said lens further comprising a collar at least partially encircling said lens body. The light module can further include at least one shoulder on which said collar is seated, a light source coupled to said hollow chamber at said distal end for providing light to said input surface of the lens. In some embodiments, the shoulder providing a seat for the lens can be in the form a sleeve disposed in the hollow chamber. In other embodiments, the shoulder can be in the form a protrusion extending from an inner wall of the chamber.

In the above light module, the lens can further include a peripheral surface for receiving at least a portion of the light entering the lens body via the input surface and for directing the received light via total internal reflection to the lens's output surface. In some such embodiments, the peripheral surface can have a truncated elliptical shape characterized by an input focus and an output focus.

In some embodiments, the housing of the lighting system can include a corrugated external surface for facilitating transfer of heat generated by at least one of the light module and the power module to an external environment. By way of example, the corrugated surface can include a plurality of fins disposed on the external surface of the housing for enhancing the surface area thereof, thereby facilitating the dissipation of heat to the surrounding environment.

In a related aspect, an endoscope system is disclosed, which includes a light guide configured to be at least partially inserted into a subject, and a handheld lighting system optically coupled to said light guide for providing light thereto. The handheld lighting system can include a handheld housing extending from a proximal end to a distal end, a light module disposed in said housing and having at least a light source for generating light, and a power module disposed within said housing and electrically coupled to said light module for providing electrical power thereto.

In some embodiments, the light module can be removably and replaceably disposed within the housing of the lighting system.

The lighting system, including the light module, of the above endoscope can be implemented in a manner discussed above.

In a related aspect, a device is disclosed, which includes a body housing at least one light guide, and a handheld lighting system that is mechanically coupled to the body to be in optical coupling with the light guide to provide light thereto. The handheld lighting system can include a removable and replaceable light module for generating light to be delivered to the light guide of the device. The handheld lighting system, including the light module, can be implemented in a manner discussed above. In some embodiments, the device can be any of an endoscope, a, illuminated surgical instrument, such as a surgical headlight, a video camera, a retractor, or a speculum.

Further understanding of various aspects of the invention can be obtained by reference to the following detailed description in conjunction with the drawings, which are described briefly below.

BRIEF DESCRIPTION OF THE DRAWINGS

FIG. 1 is a schematic perspective view of a handheld lighting system according to an embodiment of the present teachings, FIG. 3 is a schematic exploded perspective view of the handheld lighting system depicted in FIG. 1, FIG. 5A is a perspective exploded view of a light module suitable for use in a handheld lighting system according to the present teachings, FIG. 8A is a cross-sectional view of an endoscope according to an embodiment in which a lighting system according to the present teachings provide light for illuminating a field of view, FIG. 9 is a perspective view of an endoscope according to an embodiment having a lighting system according to the present teachings, where the light system receive AC line voltage, FIG. 10B is a perspective view of a lens employed in the light module depicted in FIG. 10A.

DETAILED DESCRIPTION

Figure 2A:
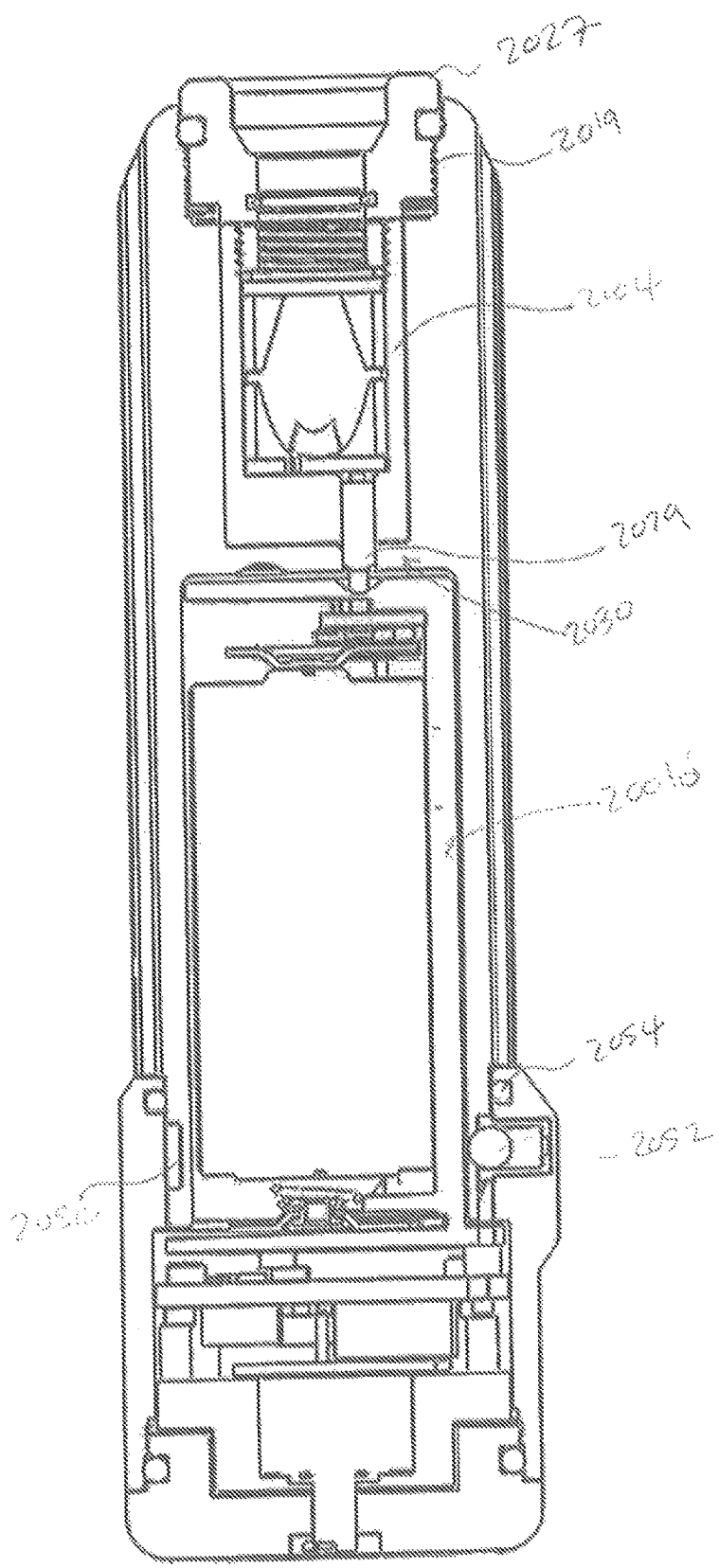
FIG. 2A is a cross-sectional view of the handheld lighting system depicted in FIG. 1.
Figure 2B:
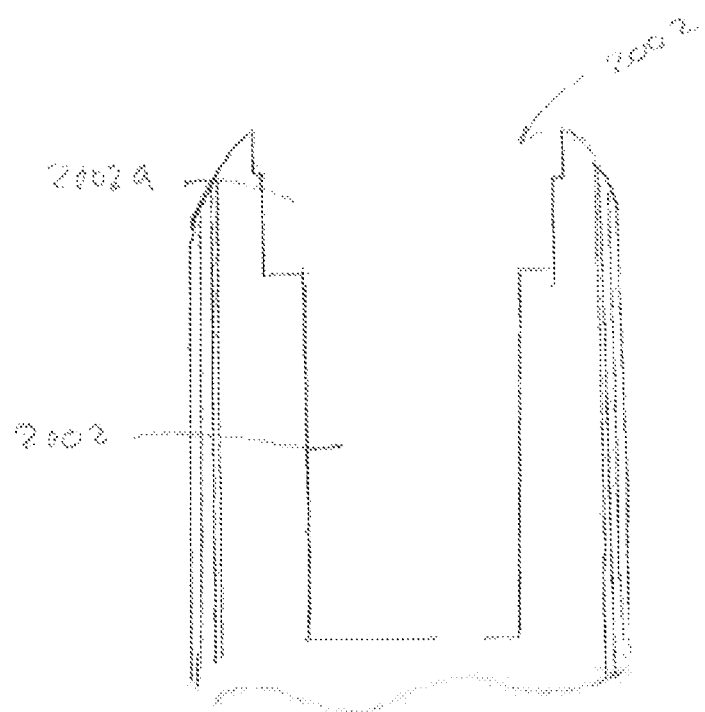
FIG. 2B is a partial cross-sectional view of a cavity provided at the distal end of the lighting system for removably and replaceably receiving a light module and an adapter for coupling the lighting system to a device for supplying light thereto.
Figure 4:
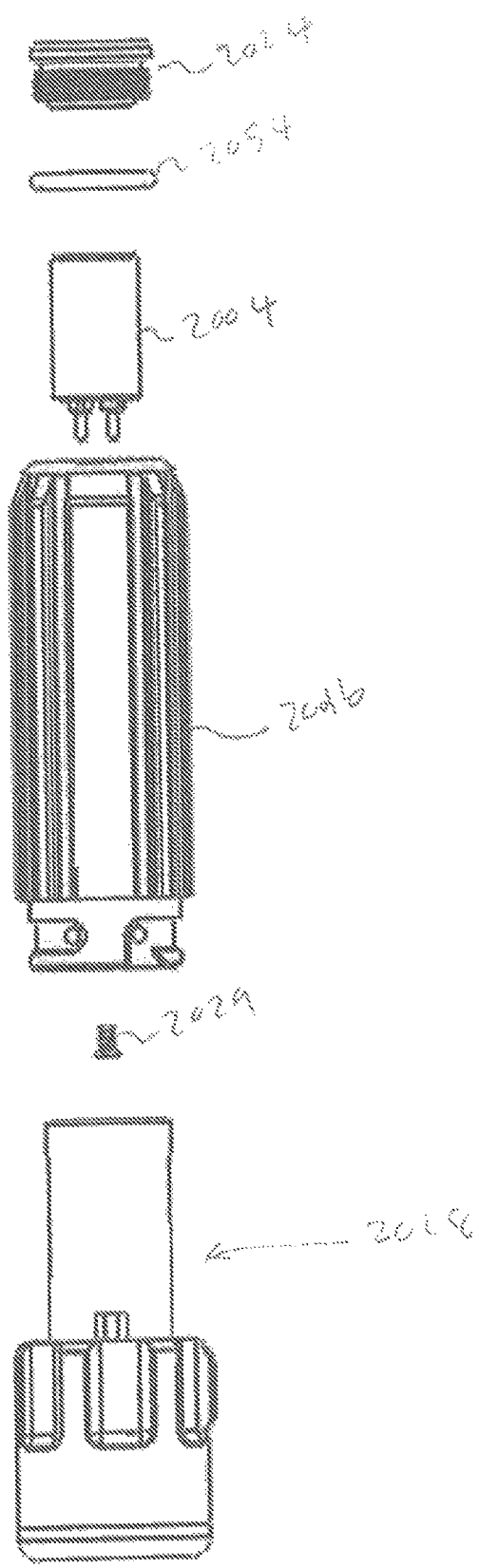
FIG. 4 is another exploded view of the handheld lighting system.
Figure 5B:
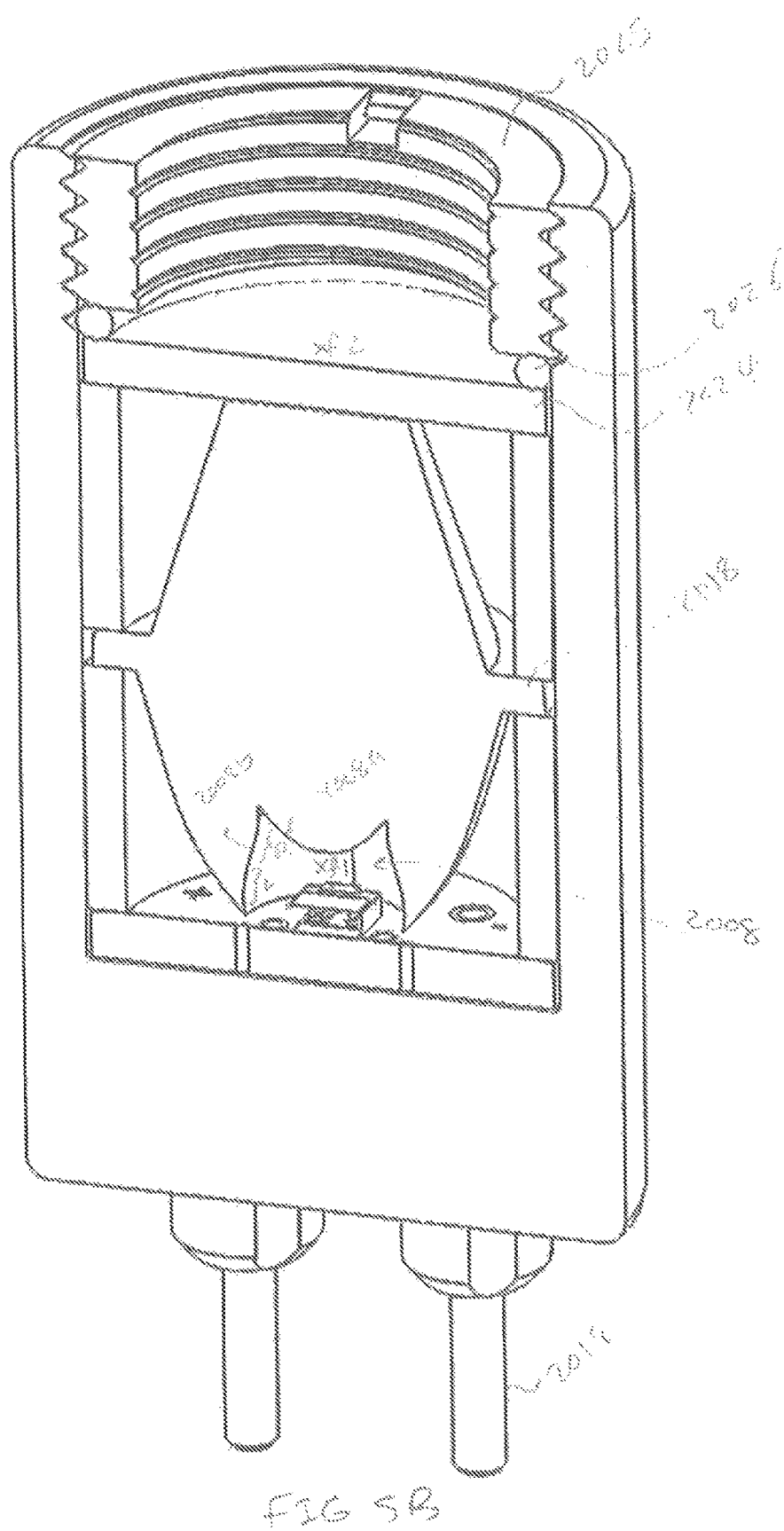
FIG. 5B is a cross-sectional view of the light module depicted in FIG. 5A.

The present invention generally relates to a handheld illumination system (herein also referred to as a handheld lighting system) that can efficiently transfer light emitted from a light source (typically an LED) to a light guide (e.g., optical fiber). In some embodiments, the illumination system can transfer light emitted by an LED to a light guide with an efficiency greater than about 30%, or greater than about 40%, or greater than about 50%, or greater than about 60%, or greater than about 70%, or greater than about 80%, or greater than about 90%, or greater than about 95%. The illumination system includes a removable and replaceable light module for generating light and a power module for supplying electrical power to the light module as well as controlling its operation. As discussed above, a handheld illumination system according to the present teachings can be coupled to a variety of different medical and industrial devices to provide light thereto. In many embodiments, at least a portion of the system's housing functions as a heat sink to efficiently dissipate heat generated by any of the light or the power module. As discussed in more detail below, the handheld illumination system can collect light emitted by a light source (e.g., an LED) over a large angular spread (e.g., a divergence angle of about 180 degrees) and converge that light into a substantially smaller angular spread to efficiently couple that light to a light guide of a device (e.g., an endoscope). Moreover, in some embodiments, the output light generated by a handheld illumination system according to the present teachings can exhibit a high color-over-angle uniformity. Various embodiments of a handheld lighting system according to the present teachings are discussed below.

Various terms are used herein consistent with their common meanings in the art. By way of further explanation, a number of terms are defined below:

The term "optical power" is used herein consistent with its common meaning in the art to refer to the degree to which an optical component or surface converges or diverges incident light and is equal to the reciprocal of the focal length of the component of the surface.

The term "elliptical surface" or similar terms as used herein refer to a surface that is shaped as a section of an ellipse. In other words, an elliptical surface is in the form of a truncated ellipse.

The term "numerical aperture" is used herein consistent with its common meaning in the art to refer to a dimensionless number that characterizes the range of angles over which an optical component or system can emit or accept light.

The term "about" as used herein is intended to indicate a variation of at most 10% around a numerical value.

The term "substantially" as used herein is intended to indicate a deviation of less than 5% relative to a complete state or condition.

With reference to FIGS. 1, 2A, 2B, 3, 4, 5A and 5B, a handheld lighting system 2000 according to an embodiment of the present invention includes a handheld housing 2001 that extends from a proximal end (PE) to a distal end (DE) and is composed of a proximal section 2001a (herein also referred to as a rotatable shell) and a distal section 2001b (herein also referred to as the heat sink portion), which are releasably coupled to one another. The handheld lighting system 2000 also includes an endcap 2001c. In this embodiment, the heat sink portion 2001b is formed of a thermally conductive material, such as aluminum, to function as a heat sink for transferrin heat generated within the housing to the external environment. In this embodiment, the rotatable shell 2001a and the endcap 2001c can be formed of a plastic, such as acrylonitrile butadiene styrene (ABS). In other embodiments, the heat sink, the rotatable shell and the endcap can be formed of the same material, e.g., aluminum.

The heat sink portion 2001b includes an enclosure 2002, which is composed of two substantially cylindrical hollow portions 2002a and 2002b with different diameters. A standalone light module 2004 is removably and replaceably disposed in the hollow portion 2002a. The light module 2004 includes a housing 2005 in which various components of the light module are disposed. In particular, the light module 2004 includes a lens 2006 having a proximal section 2006a with an input surface 2008 that forms a cavity for receiving light from a light emitting diode 2010, which is mounted on a printed circuit (PC) board 2012. In this embodiment, the input surface includes a central convex portion 2008a surrounded by a peripheral portion 2008b, where the peripheral portion 2008b includes a proximal concave segment (A) and a distal convex segment (B). In some embodiments, the central convex portion 2008a can exhibit an optical power in a range of about 50 D to about 300 D.

In this embodiment, the central convex portion of the input surface provides a positive optical power, which results in the convergence of the light rays entering the lens body through that surface to a focal point (herein also referred to as the convergence point) typically located within the lens body, e.g., a small distance below the lens' output surface. In some other embodiments, the convex portion is configured such that its focal point (i.e., the point at which the light rays refracted by that portion converge) is external to the lens. By way of example, the focal point of the convex portion may be within the proximal end of a light guide coupled to the lens, or external to both the lens and the light pipe such that the light rays diverging form the focal point to illuminate the input face of the light pipe would exhibit a maximum angular spread corresponding to that of a solid angle subtended by the input face of the light guide. By way of example, in some such embodiments, the focal point of the convex portion can be substantially coincident with the distal focal point of the elliptical peripheral surface.

The proximal portion 2006a further includes an elliptical peripheral surface 2016 that directs the light incident thereon via total internal reflection to the output surface of the lens 2014. The lens 2006 further includes a distal section 2006b having an output surface 2014 through which the light exits the lens and a peripheral surface 2013, which is in the form of a truncated cone in this embodiment, though other shapes can also be utilized.

The peripheral elliptical surface 2016 is characterized by an input focal point f1 and an output focal point f2, which are positioned on the optical axis (OA) of the lens in this embodiment. The peripheral elliptical surfaces transfers at least a portion of the light emitted by the light source 2010 from the input focal point to the output focal point. In this embodiment, the input focal point is positioned within the input cavity and the output focal point is positioned external to the lens at a distance relative to the output surface of the lens. In some embodiments, the position of the output focal point is selected such that the light rays diverging from the output focal point exhibit an angular spread across the input face of a light guide coupled to the lens that maximizes the coupling of the light into the light guide. For example, the diverging beam can have an angular spread commensurate with an input numerical aperture of the light guide. For example, the distance between the output focal point 1240 and the output surface of the lens may be in the range of about 4 mm to about 6 mm, though other values can also be used depending, for example, on the lens size and/or particular application in which the lens is employed.

A plurality of leads 2017a/2017b allow coupling the light module to a power module 2028, which is described in more detail below. A pair of sleeves 2013a/2013b protect the leads 2017a/2017b.

The lens 2006 further includes a collar 2018 (herein also referred to as a flange) that encircles the lens body. While in this embodiment the collar 2018 partially encircles the lens body, in other embodiments, the collar can fully encircle the lens body. The lens 2006 is mechanically secured over the PC board 2012 via a pair of sleeves 2020 and 2022 (herein also referred to as spacers) disposed, respectively below and the above the lens collar 2018 and in contact therewith. An optical window 2024 is disposed over the output surface 2014 of the lens and is supported by the sleeve 2022.

The optical window 2024 is preferably in contact with the output surface 2014 of the lens to ensure good optical coupling between the window and the lens. In some embodiments, a refractive index matching material, such as a gel, may be disposed between the output surface of the lens and the optical window to minimize optical loss as light exiting the lens couples into the window to pass therethrough. The optical window 2024 can protect the output surface of the lens. In addition, in some embodiments, the optical window 2024 can adjust one or more characteristics of the light exiting the lens. By way of example, the optical window 2024 can be selected to function as a filter, e.g., a bandpass filter, to allow passage of certain wavelengths of the light exiting the lens while blocking other wavelengths. For example, such filtering of the light exiting the lens can be used to adjust the color temperature of the light. The optical window 2024 can be formed of a variety of different materials, such as sapphire, quartz, glass, etc. In some embodiments, the material from which the optical window 2024 is formed is substantially transparent to visible radiation. In other embodiments, the optical window 2024 may be substantially transparent to radiation in another region of the electromagnetic spectrum. By way of example, in some embodiments in which the light module emits radiation in the infrared region of the electromagnetic spectrum, the optical window 2024 can be formed of high density polyethylene.

The light module 2004 further includes a retaining window 2025 (herein also referred to as ring window) that is removably and replaceably attached to the upper end of the light module's housing 2005. In particular, in this embodiment, the window ring 2025 includes a plurality of external threads 2025a that can engage with a plurality of internal threads 2005a provided at the upper end of the module's housing. A gasket 2026 is disposed between the retaining window and the optical window. The retaining window, the optical window and the gasket cooperatively seal the light module from the external environment.

The handheld lighting system 2000 further includes an adapter 2027 (herein also referred to as "light guide adapter") that can be removably and replaceably received in the upper hollow cylindrical portion 2002b of the enclosure 2002 provided proximate the distal end of the housing 2001 to allow coupling the lighting system to a plurality of different devices employing, for example, light guides for illuminating a field of view. In this embodiment, the light guide adapter can include a plurality of threads 2027a that can engage with a plurality of threads 2019 provided in the inner wall of the upper hollow cylindrical portion 2002b. In other embodiments, the light guide adapter 2027 can be snapped into the enclosure 2002b. A gasket 2011 is positioned between the adapter 2027 and the light module 2004 to provide a seal therebetween.

Advantageously, the handheld system 2000 can be coupled to a variety of different devices, e.g., by simply changing the light guide adapter 2027, to provide light to light guides employed in such devices for illuminating a field of view. Some examples of such devices include, without limitation, endoscopic systems, illuminated surgical instruments, such as a surgical headlight, a video camera, a retractor, a speculum, and other devices requiring high intensity, high quality light.

Figure 6:
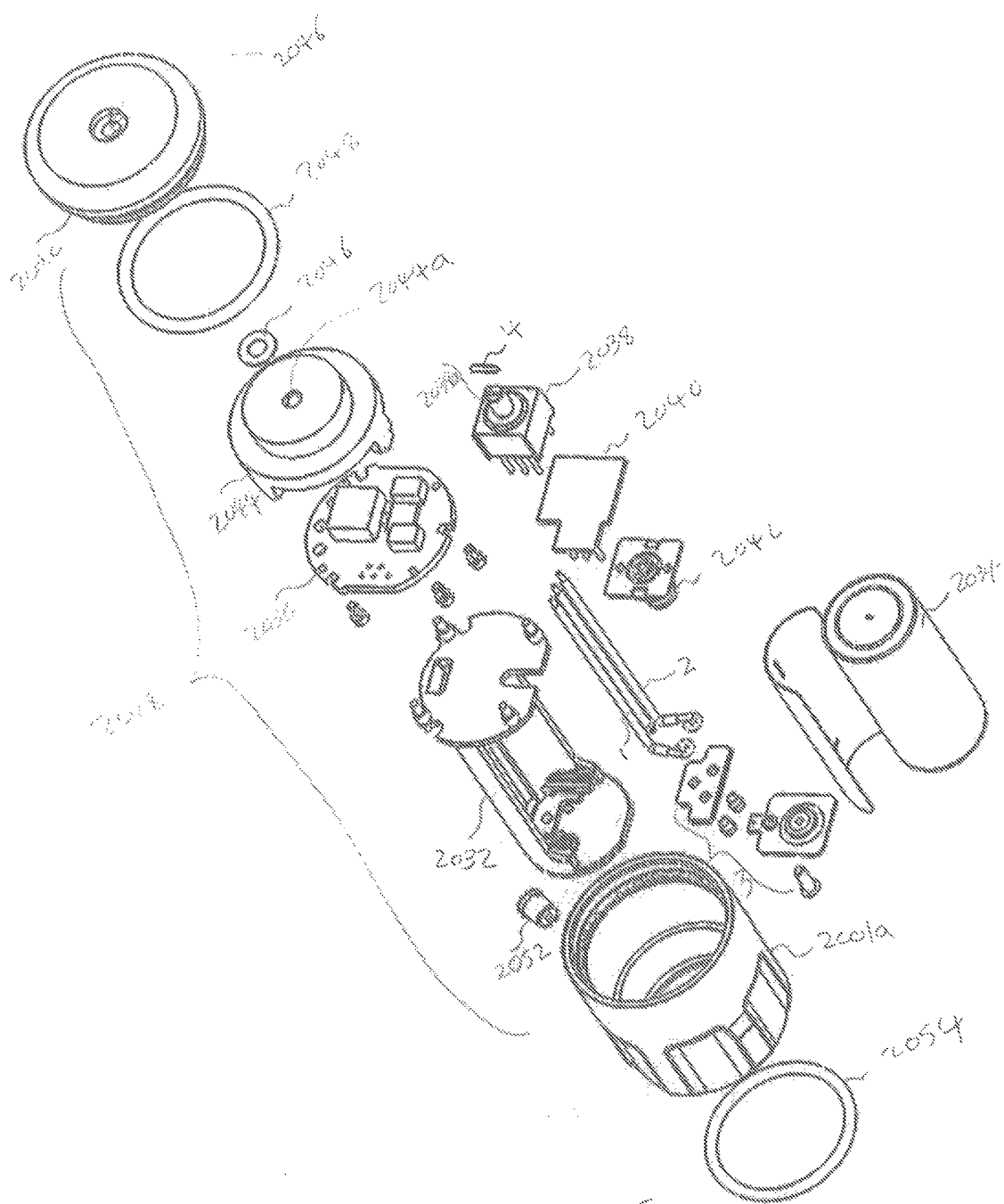
FIG. 6 is an exploded view of the power module of the a handheld lighting system according to an embodiment of the present teachings depicting its various components.
Figure 7:
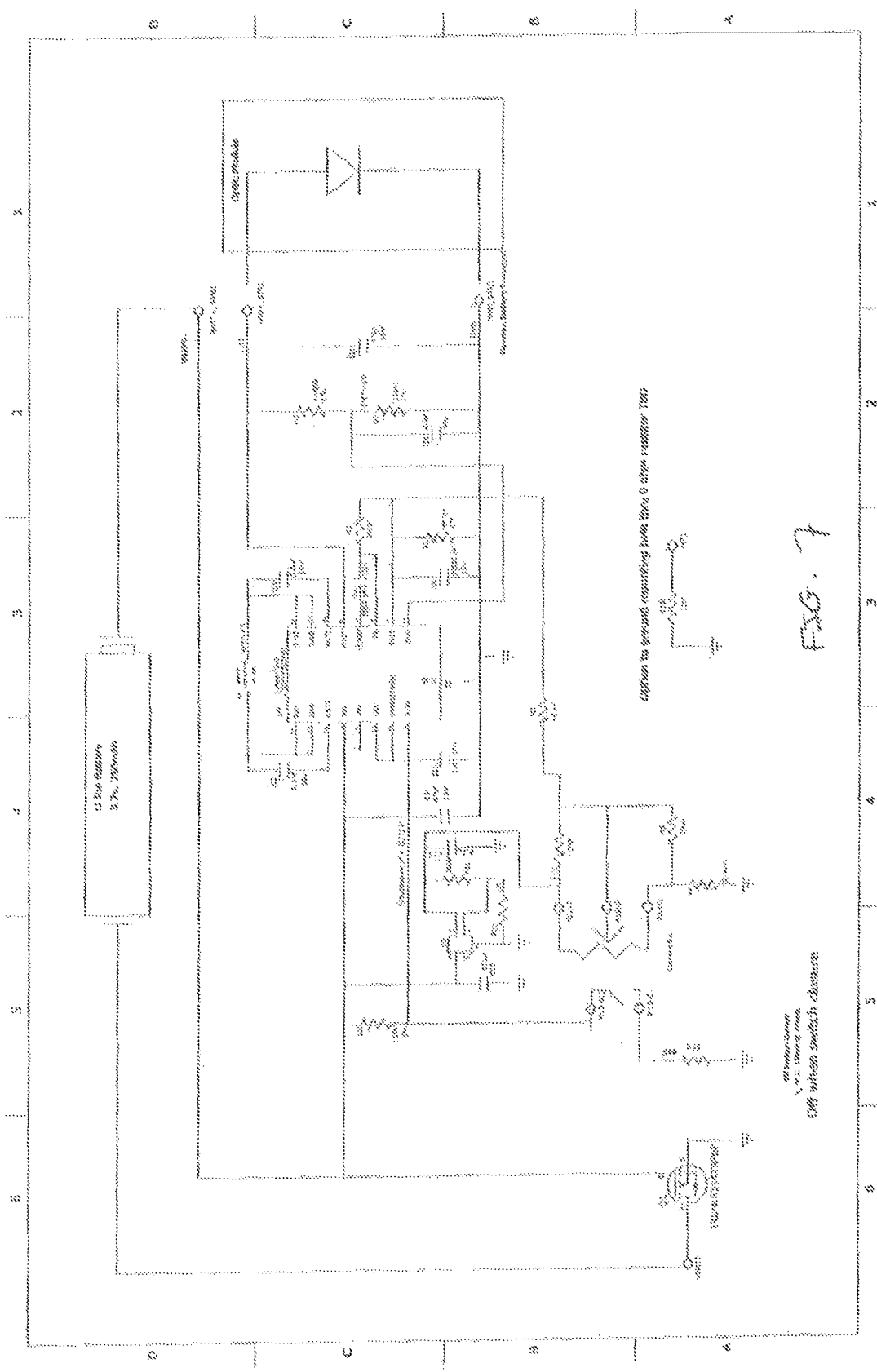
FIG. 7 is an exemplary circuit diagram of the power module for adjusting the intensity of an LED employed in the lighting system.

With reference to FIGS. 2A, 3, and 6, the handheld lighting system 2000 further includes the power module 2028 that is disposed in the housing 2001 to provide electrical power to the light module 2004 and control its operation. More specifically, in this embodiment, a portion of the power module is accommodated within the rotatable shell 2001a and another portion thereof is accommodated within a hollow enclosure 2000d provided within the heat sink portion 2001b of the housing 2001. In this embodiment, the power module 2028 is secured to the housing via a screw 2029 that protrudes through an inner wall 2030 of the housing.

The power module 2028 includes a casing 2032 (herein also referred to as a sled) for housing at least a battery 2034 for providing power to the LED 2010. The power module 2028 further includes a printed circuit board 2036 on which electronic components for controlling the operation of the light module are mounted, as discussed in more detail below. In particular, a potentiometer/switch 2038 is mounted on a switch printed circuit board 2040, which is in turn mounted on the PC board 2036. A spring 2042 facilitates forming an electrical contact with the battery 2034 when the switch 2038 is used to switch on the illumination system. The potentiometer 2038 includes a shaft 2038a that allows adjusting its Ohmic resistance, which in turn allows adjusting the intensity of the light emitted by the LED 2010, as discussed in more detail below.

The power module 2028 further includes a printed circuit board mount 2044 having an opening 2044a through which the shaft of the potentiometer can extend. In addition, the shaft of the potentiometer extends into an opening 2046 provided within the endcap 2001c of the housing to rotatably couple the potentiometer's shaft to rotatable shell 2001a. A spacer 2046 and a static seal 2048 are disposed between the housing end cap 2001c and the PC board mount 2044, where the static seal helps sealing the power module from the external environment.

In this embodiment, the rotatable shell 2001a is rotatably coupled to the heat sink portion 2001b of the housing. More specifically, the outer wall of the heat sink portion includes a circumferential groove 2050 at its proximal end, where the groove extends 300 degrees around the housing. The rotatable shell 2001a includes a spring loaded ball 2052 that can engage with the groove 2050. The groove 2050 includes a detent mechanism at each of its extreme ends for capturing the ball thereby limiting the rotation of the rotatble shaft.

A user can apply a rotational torque to the rotatable shell 2001a to disengage the spring loaded ball from the detent mechanism and rotate the shell, which in turn causes the rotation of the potentiometer's shaft via the endcap 2046. The rotation of the potentiometer's shaft can cause a change in its resistance, which in turn results in adjusting the intensity of the light emitted by the LED 2010. In this embodiment, a piece of wire 4 disposed in a groove of the potentiometer shaft 2038a helps with coupling of the shaft to the endcap 2046.

A dynamic seal 2054 is provided between the rotatable shell 2001a and the heat sink portion 2001b to facilitate sealing the various components within the housing while allowing the rotation of the shell 2001a for adjusting the intensity of the light emitted by the LED 2010.

With continued reference to FIG. 5, the power module 2028 further includes a pair of wires 1 and 2, and the associated components 3 that allow forming an electrical contact between the battery 2034 and the circuit board 2036.

FIG. 6 schematically shows a circuit diagram of the electronic components within the power module 2028, at least some of which are mounted on the PC board 2026, supplying electric power to the LED 2010 and adjusting the intensity of the emitted light. As noted above, the battery 2034 provides electrical power for the LED 2010. In this embodiment, the battery provides a voltage of 3.7 volts and 750 milliamperes of current. A transistor Q1 provides protection against positioning the battery in a reverse direction. A switch (R13-NC/R13C) allows switching the power to LED 2010. The potentiometer (R13-1, 2, 3) adjusts the current applied to the LED 2010 by shunting current from the feedback network (R1, R2, R3, C4, and C6). The output current (Iout) of the switching regulator U1 (LTC3112EDHD) mirrors the LED current, where U1 can ramp up the LED current until the voltage at the FB pin reaches the feedback voltage. A low-drop-out voltage regulator U2, R20, and R21 set a stable voltage so that U1 can regulate the LED current all the way to zero (e.g., to keep the current properly regulated as the battery voltage drops). The resistor R4 sets the upper limit on the LED current (about 1.03 A). The value of this resistor can be increased to limit the LED current to less than 1 A. In this embodiment, the capacitor C5 and the resistors R6 and R7 set the maximum output voltage to 6 V, which limits the voltage when the LED is not installed in the handheld system. Further, U1 and the inductor L1 handle the buck/boost switching to maintain the LED current in face of falling battery voltage.

As noted above, the heat sink portion 2001b not only provides a housing for the light module and a portion of the power module, it also facilitates the transfer of heat generated by one or more components within the housing to the external environment, thereby ensuring that the temperature of outer surface of the housing remains below a desired threshold. With reference to FIGS. 1 and 3, the outer surface of the heat sink portion 2001b of the housing 2001 includes a plurality of fins 2064, which facilitate the transfer of heat generated by one or more components within the housing (e.g., the LED 2010) to the external environment. More specifically, the fins 2064 increase the external surface area of the heat sink portion, thereby enhancing the dissipation of heat to the external environment. In this embodiment, the fins 2064 are disposed longitudinally along the outer surface of the heat sink portion (i.e., parallel to an optical axis (OA) of the illumination system). The use of longitudinal fins can also provide manufacturing advantages as it allows the fabrication of the housing using extrusion techniques.

While in this embodiment, twelve fins are employed, the number of fins in other embodiments can be different. In some implementations, the depths of the valleys between adjacent fins (or in other words the heights of the fins) can be, for example, in a range of about ⅛ inches to about ⅙ inches. In some embodiments, the total effective surface area of the external surface of the heat sink portion, i.e., the area effective in dissipating heat, can be at least about 10 square inches. In some implementations, the efficiency of heat dissipation by the heat sink ensures that the temperature of the outer surface of the housing remains below about 115° F. when the lighting system is in use. In some cases, maintaining the temperature of the housing at or below the maxiumum temperature can be achieved even when the LED 2010 is operated at a current of 1 ampere.

In some embodiments, not only the heat sink portion 2001b but also the rotatable shell 2001a can be formed of a thermally conductive material, e.g., a metal such as aluminum, to facilitate transfer of heat generated by one or more components within the housing to the external environment. Further, in such embodiments, the rotatable shell can include a plurality of fins for enhancing heat dissipation.

Figure 8B:
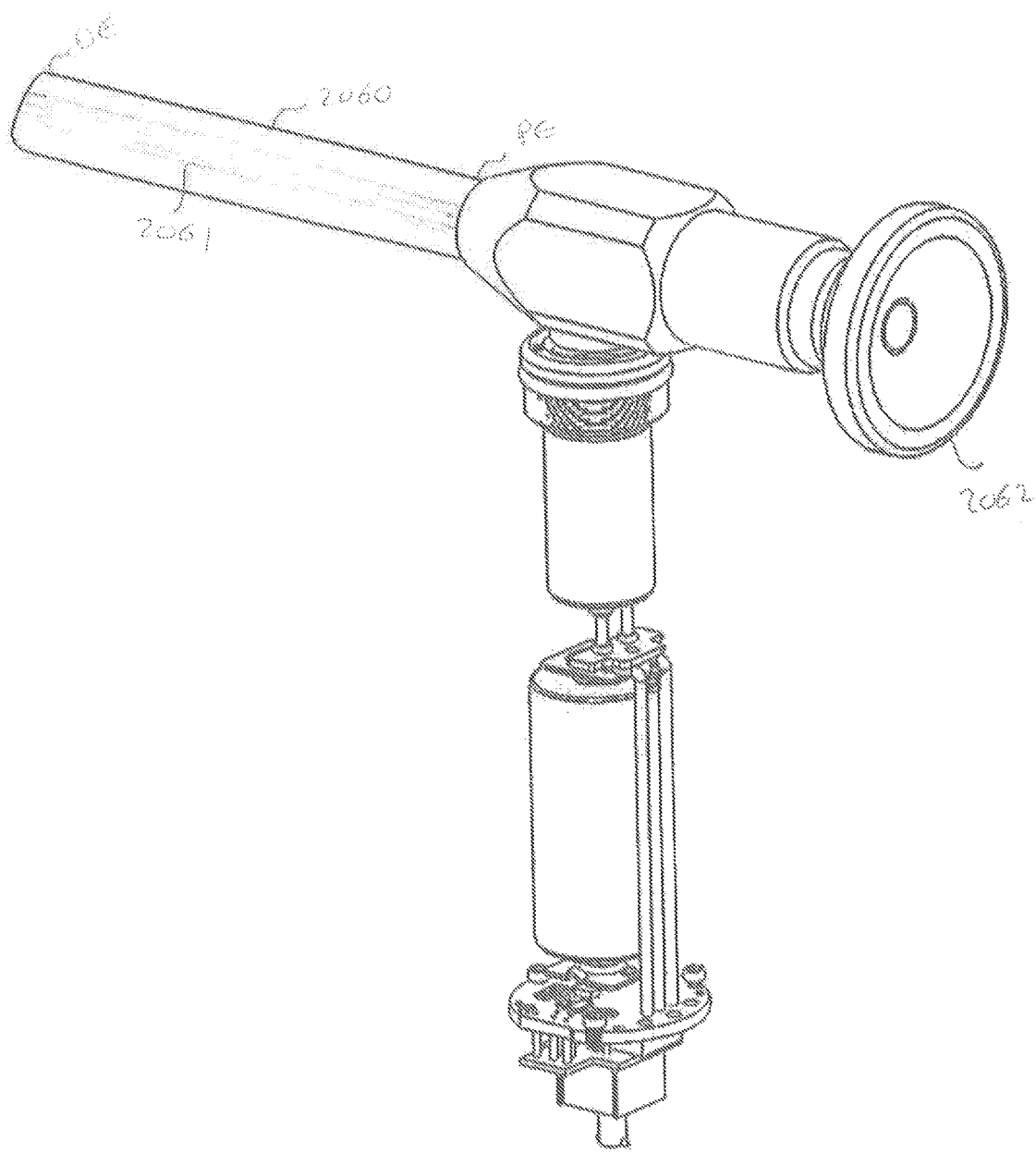
FIG. 8B is perspective view of the endoscope depicted in FIG. 8A.

As noted above, in some embodiments, the handheld illumination system can be coupled to a medical or industrial device to provide light, for example, to one or more light guides of the device for illuminating a field of view. By way of example, FIGS. 8A and 8B schematically depict an endoscope 2056 having an endoscope body 2058 including a flexible elongated element 2060 extending from a proximal end (PE) to a distal end (DE) in which a plurality of optical fibers 2061 are disposed. The endoscope 2056 can also include other optical components such as one or more lenses, cameras, and image processing circuitry (not shown in the figure) in a manner known in the art. The elongated element is configured for insertion into a patient. The exemplary endoscope 2056 also includes a handle 2062 for manipulating the device.

The handheld illumination system 2000 according to the present teachings is coupled to the endoscope body so as to provide light to the optical fibers disposed in the flexible element 2060. More specifically, the handheld illumination system 2000 is coupled to the endoscope body via the light guide adapter 2027. A light guide connector 2063 can facilitate optically coupling the light module 2004 to the optical fibers to provide light to the optical fibers, which can in turn transmit the light to the distal end (DE) of the flexible elongated element 2060 for illuminating a field of view.

In use, the flexible element 2060 can be at least partially inserted into a patient and the external illumination system 2000 can be employed to provide light to the light guide(s) disposed in the elongated element 2060, which in turn guide the light to the distal end of the elongated element through which the light exits the endoscope to illuminate a field of view.

While in some embodiments, a handheld lighting system according to the present teachings can be battery operated, in other embodiments the handheld lighting system can be supplied with AC line power. By way of example, FIG. 9 schematically depicts an endoscope 3000 according to an embodiment of the present teachings, which includes a handheld lighting system 3002 that is powered by AC (alternating current) line voltage. The handheld lighting system 3002 is similar to the handheld lighting system 2000 discussed above except that its power module includes an AC-to-DC converter that converts the AC line voltage to an appropriate DC voltage for application to an LED of a light module disposed in the housing.

Figure 10A:
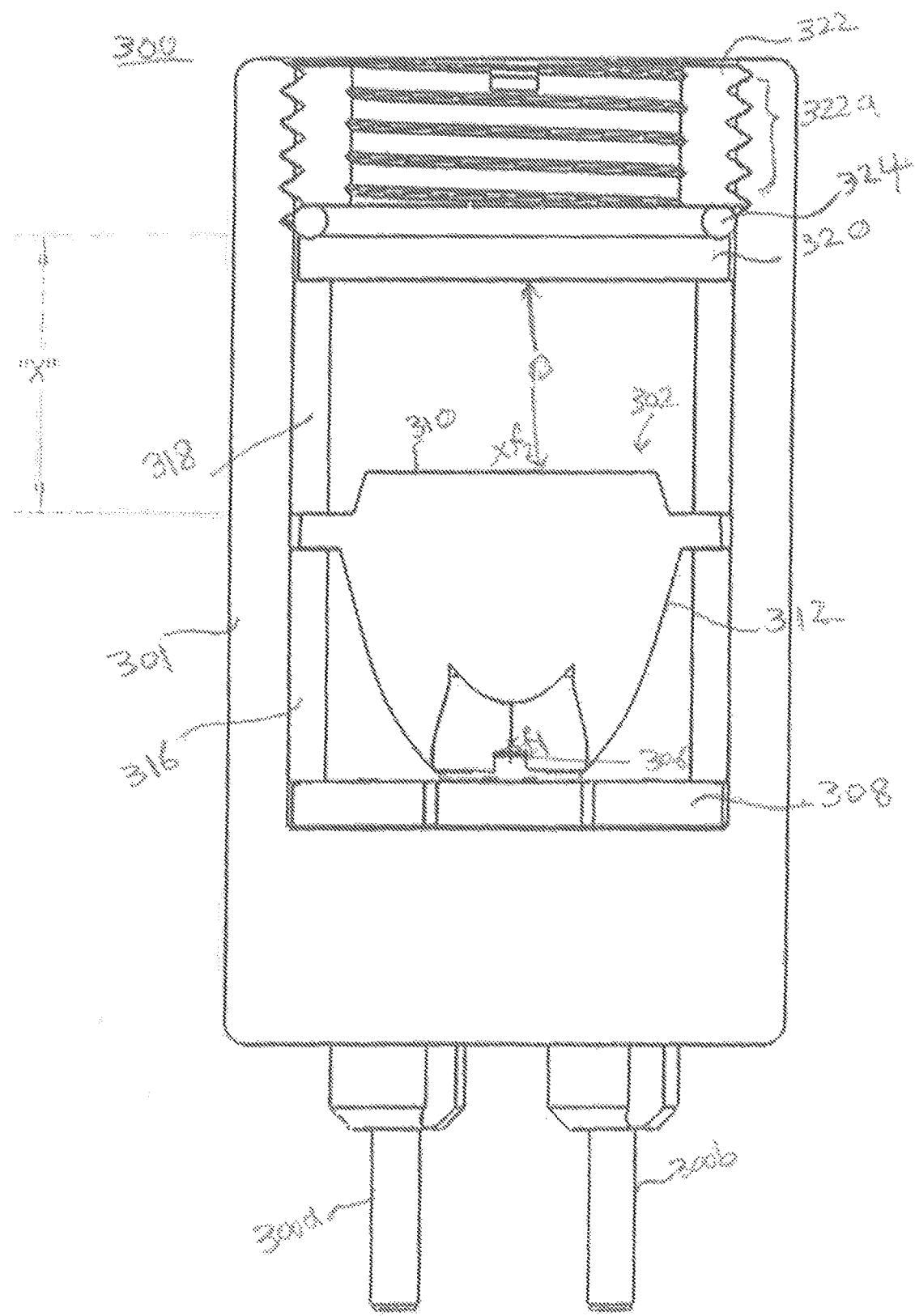
FIG. 10A is a cross-sectional view of another light module that can be employed in a lighting system according to the present teachings.
Figure 11:
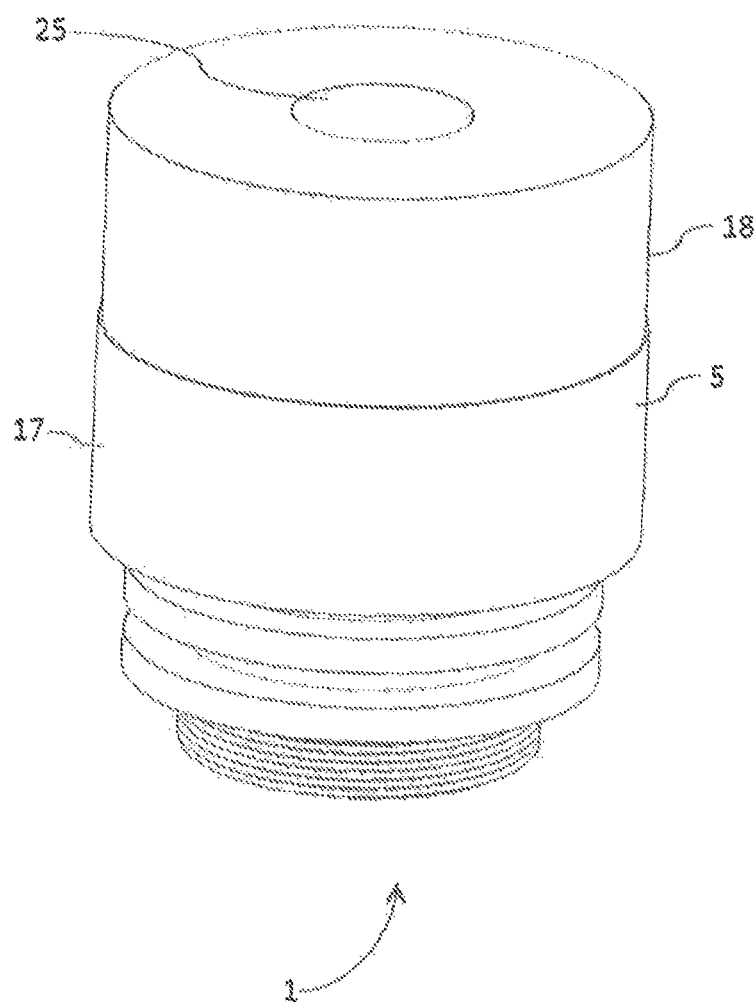
FIG. 11 is a top perspective view of a light module according to another embodiment.
Figure 12:
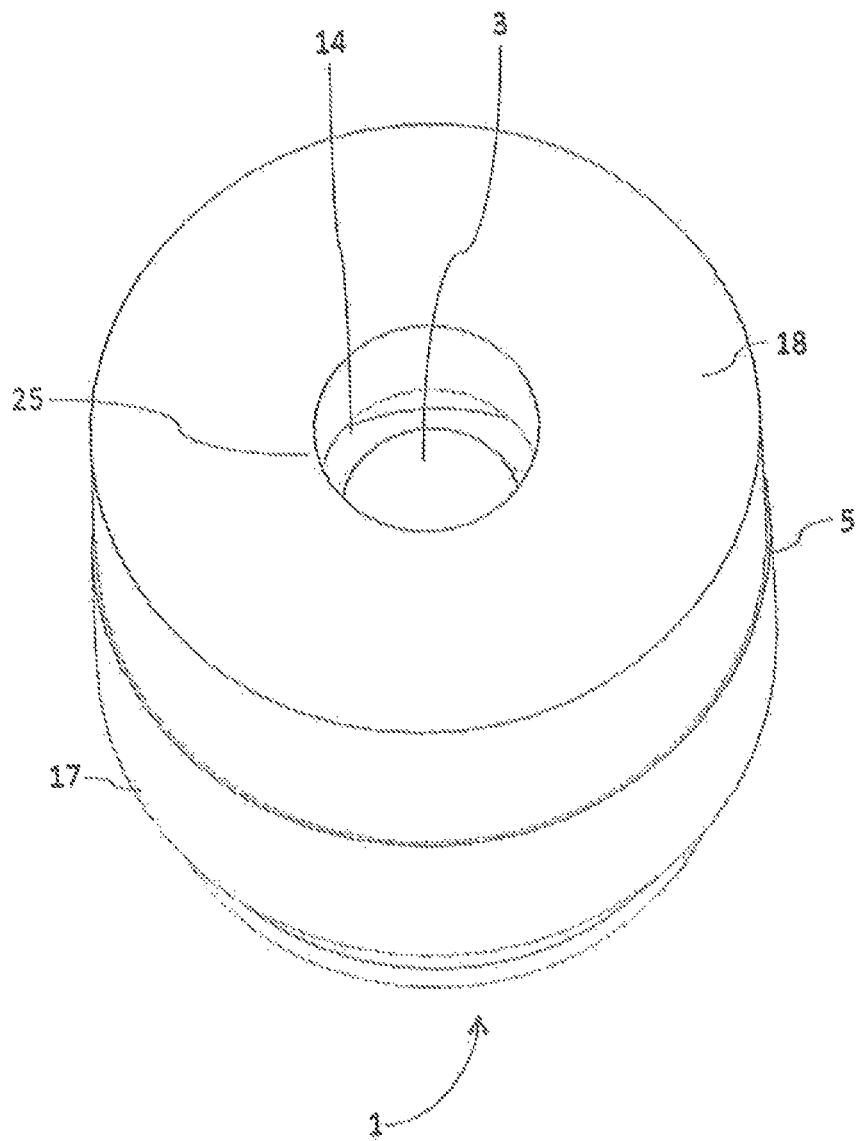
FIG. 12 is another top perspective view of the light module depicted in FIG. 11.
Figure 13:
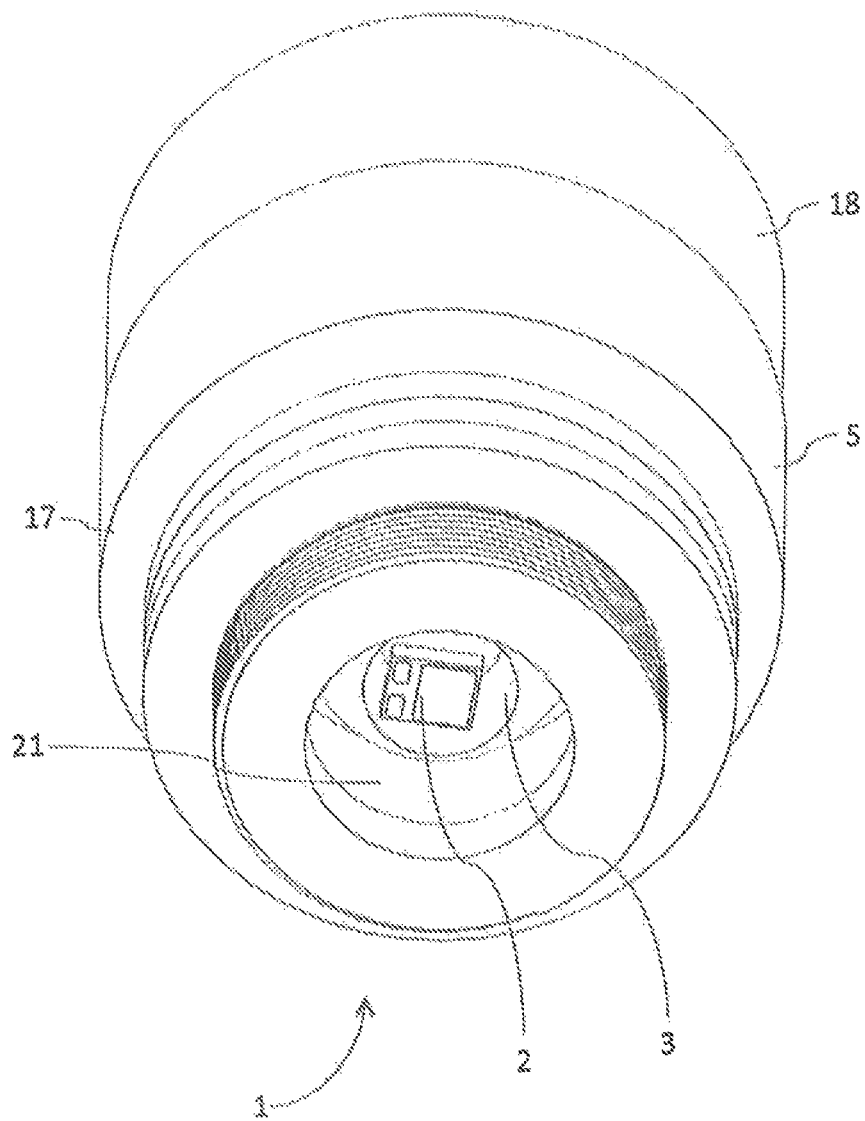
FIG. 13 is a bottom perspective view of the light module depicted in FIG. 11.
Figure 14:
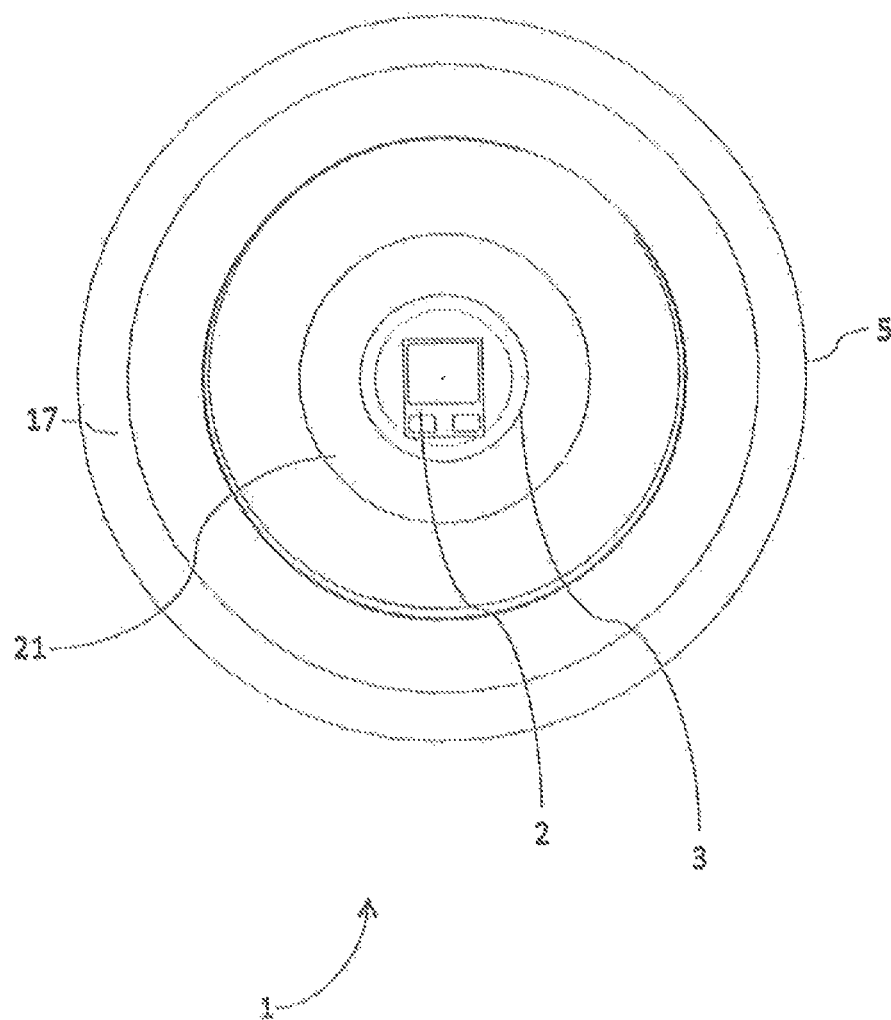
FIG. 14 is a bottom view of the light module depicted in FIG. 11.
Figure 15:
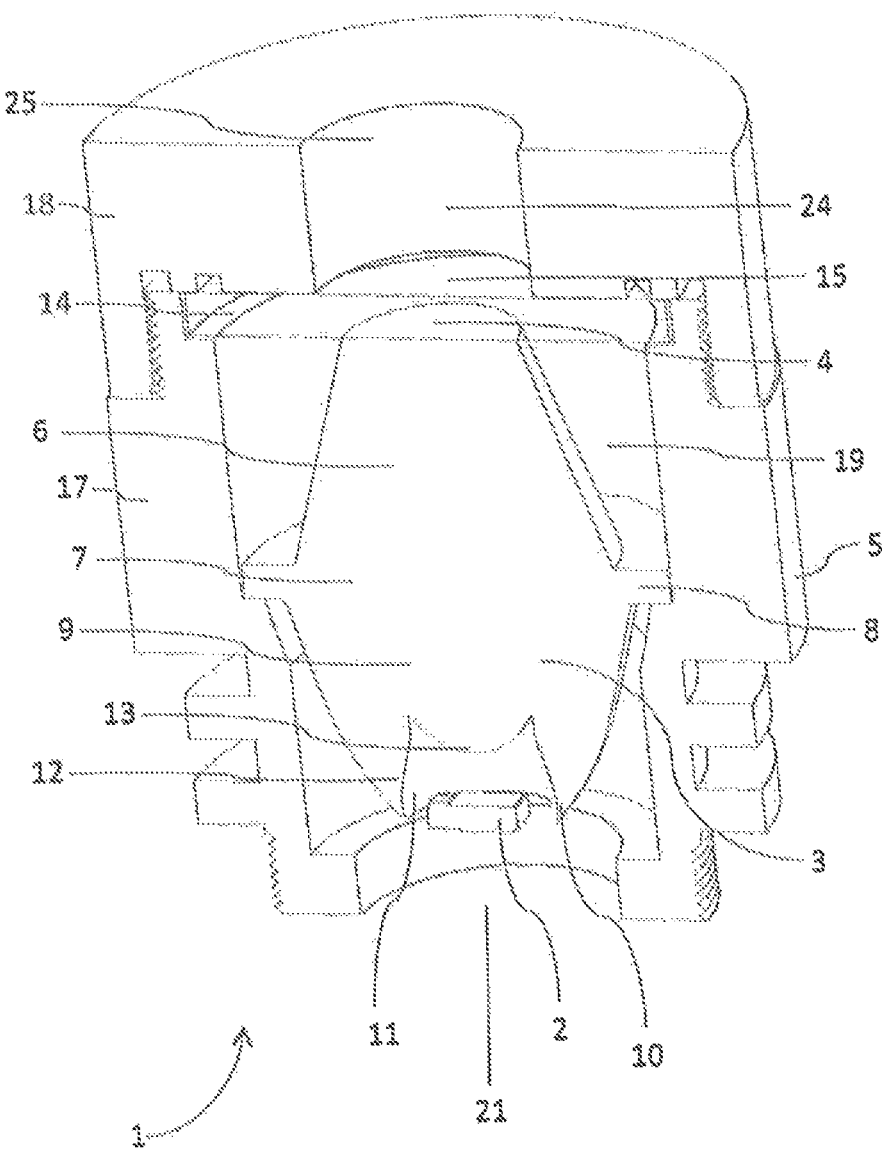
FIG. 15 is a perspective cross-sectional view of the light module.
Figure 16:
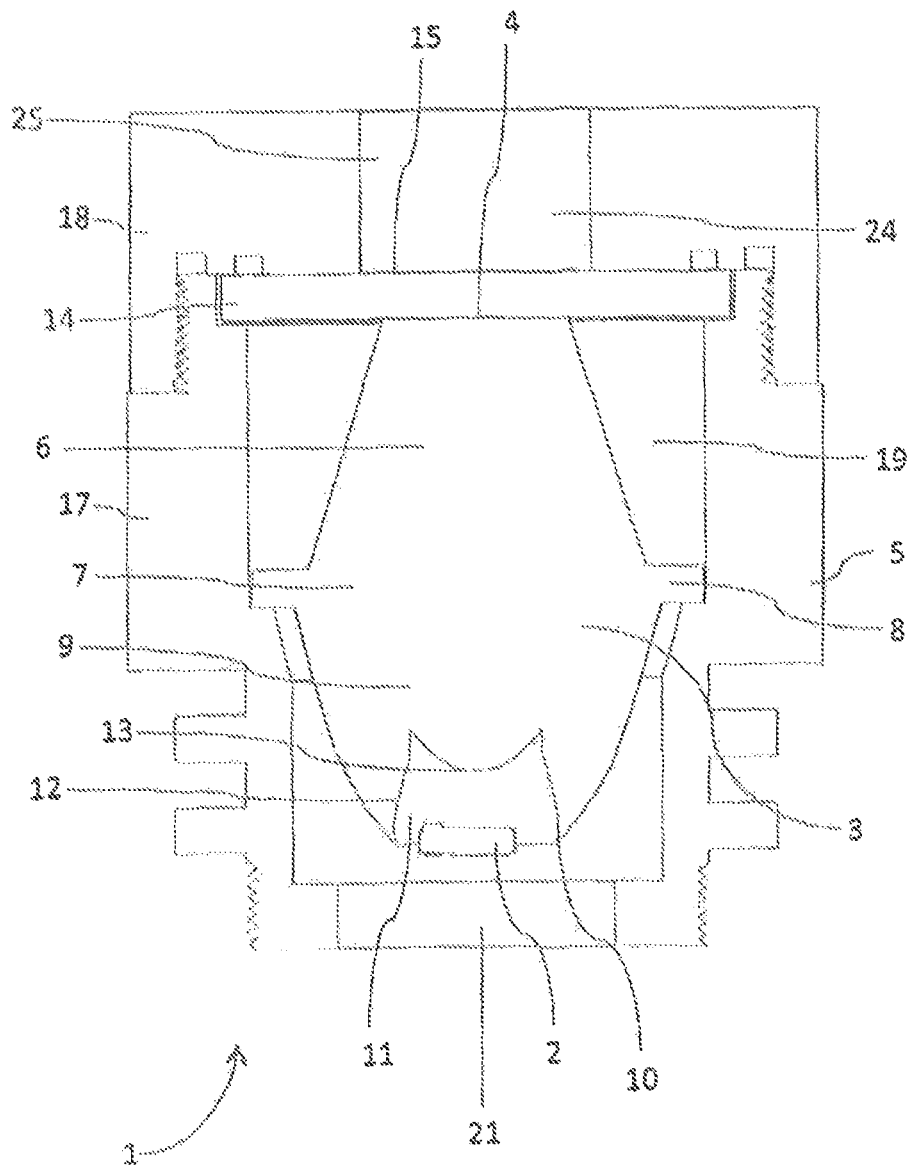
FIG. 16 is a cross-sectional view of the light module.
Figure 17:
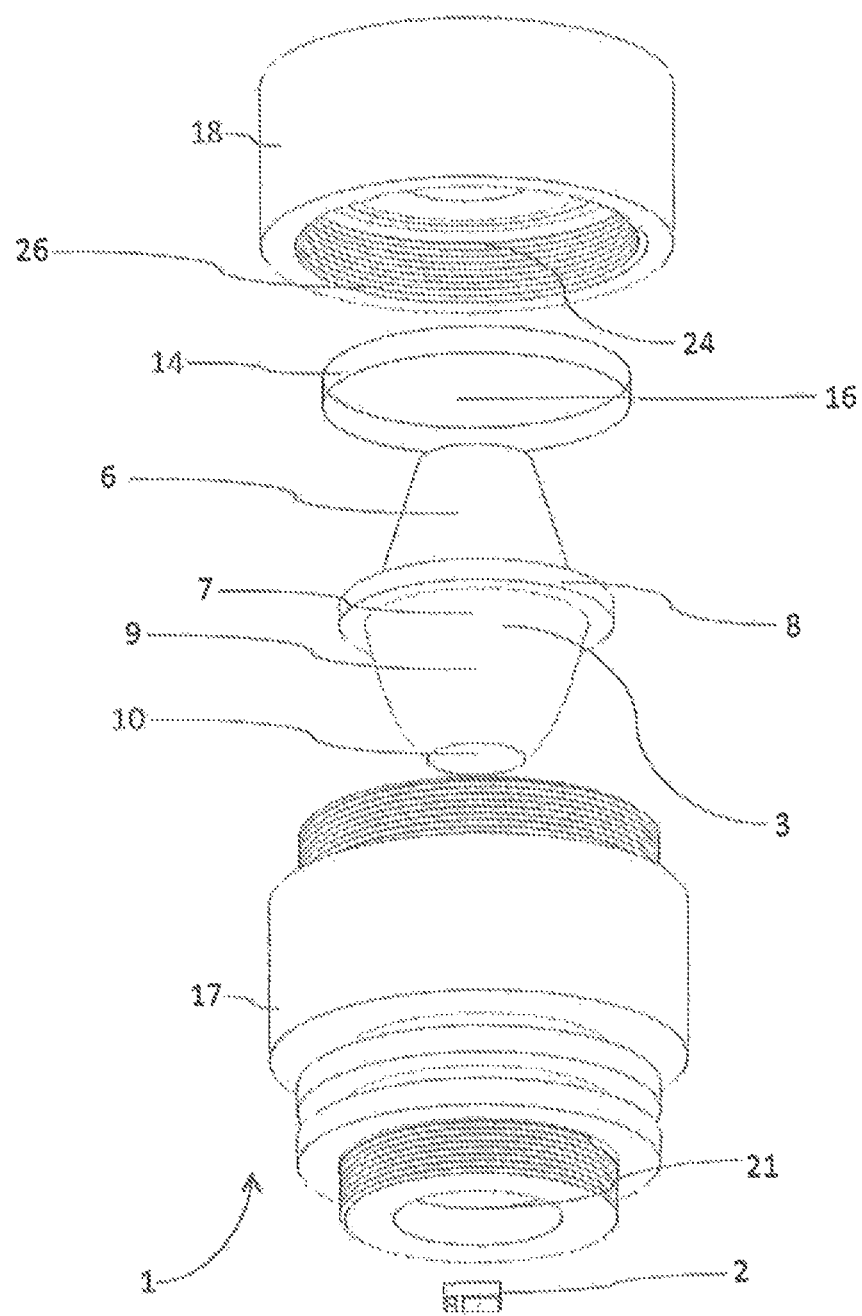
FIG. 17 is a perspective exploded view of the light module.
Figure 18:
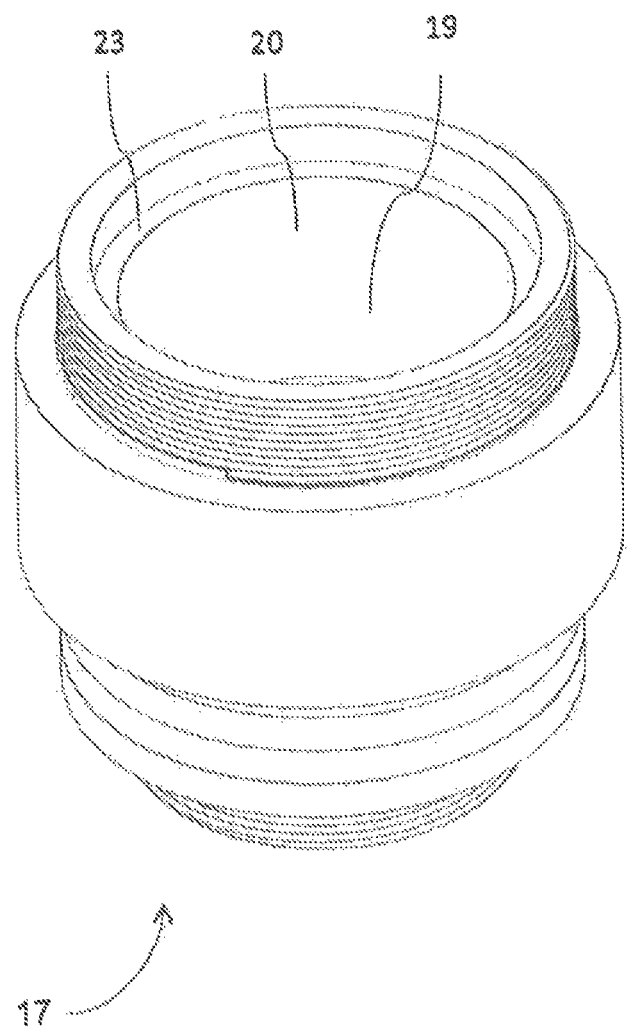
FIG. 18 is a top perspective view of a portion of the housing of the light module configured for holding the lens.
Figure 19:
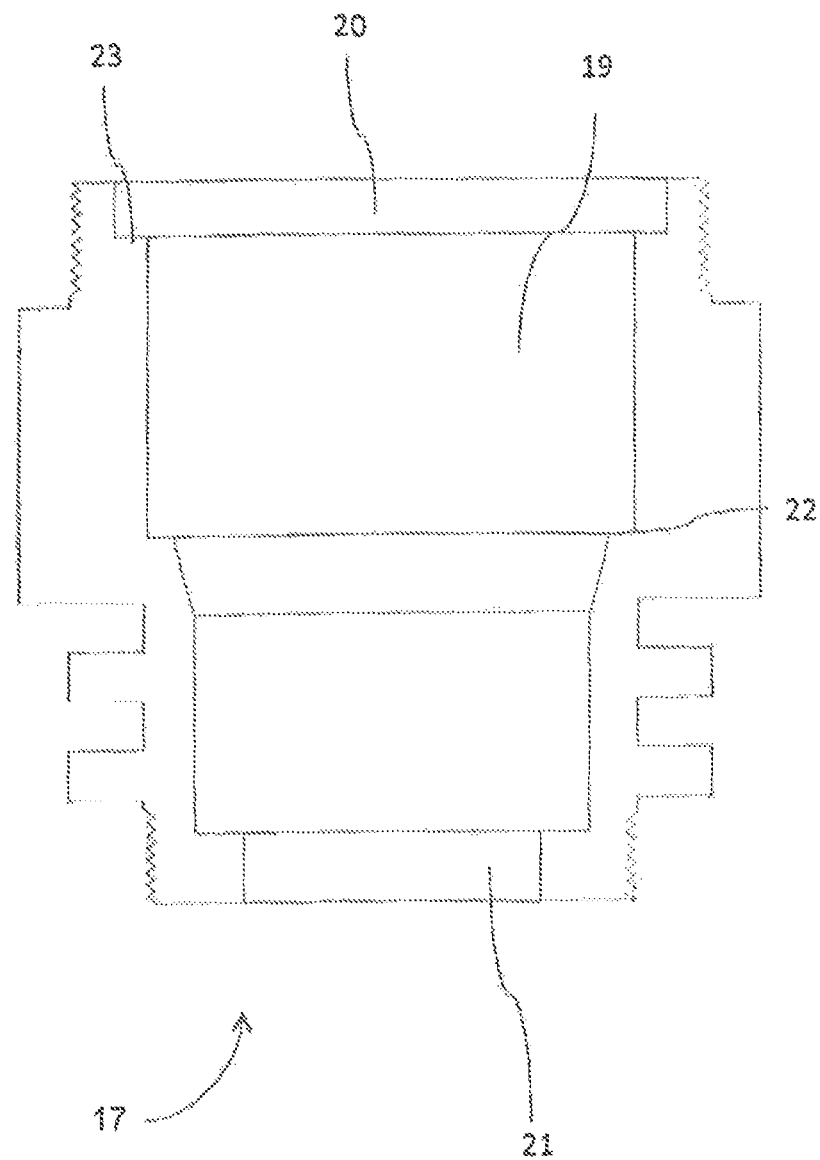
FIG. 19 is a side cross-sectional view of the lens holder depicted in FIG. 18.

One advantage of a handheld lighting system according to the present teachings is that it can be used with a variety of different light modules. For example, with reference to FIGS. 10A and 10B, a light module 300 according to another embodiment includes a housing 301 in which a lens 302 can be removably and replaceably positioned. The lens 302 includes an input surface 304 that is optically coupled to an LED 306, which is mounted on a printed circuit board 308, to receive light therefrom. The lens 302 further includes an output surface 310 (which is substantially flat in this embodiment) through which light exits the lens. The lens 302 also includes a peripheral surface 312 that receives at least a portion of the light entering the lens through its input surface and directs the light incident thereon via total internal reflection to the output surface. Similar to the previous embodiment, the peripheral surface 312 is in the form of a truncated ellipse that includes an input focus f1 on or in close proximity of the LED 306 and an output focus f2 that is external to the lens at a distance, e.g., in a range of about 4 mm to about 6 mm, above the lens' output surface 310. A collar (herein also referred to as flange) 314 partially encircles the lens body and facilitates the positioning of the lens within the housing 301, as discussed in more detail below.

More specifically, a sleeve 316 in contact with a lower surface of the collar 314 supports the lens 312 above the printed circuit board 308. Another sleeve 318 is seated on an upper surface of the lens collar 314 and supports an optical window 320 at a distance D above the output surface 310 of the lens. The optical window 320 can be implemented, for example, in a manner discussed above in connection with the previous embodiment.

A retaining window 322 is releasably coupled to the housing via a plurality of threads 322a, which engage with respective threads provided in the inner surface of the housing 301. A gasket 322 positioned between the retaining window 322 and the optical window 320 can provide a seal. Similar to the previous embodiment, the retaining window 322 can be connected to an adapter 326 of a light guide (not shown) for optically coupling the light module 300 to the light guide. The light module 300 includes a pair of electrical leads 300a and 300b for connecting the light module to a source of electrical power, such as one or more batteries.

In some embodiments, a handheld lighting system according to the present teachings can include a light module having a housing that provides a shoulder, e.g., in the form of a protrusion extending from an inner wall of the module's housing, for seating a lens. By way of example, with reference to FIGS. 11-19, a light module 1 according to the another embodiment, which can be removably and replaceably inserted within the housing includes an external housing 5 having a lens holder 17 and a window ring 8, which are releasably coupled to one another. In this embodiment, the lens holder 17 contains a cylindrical internal channel 19 with a top opening 20 and a bottom opening 21. The lens holder 17 contains an internal shoulder 22 for holding an optical lens 3 within the internal channel 19. The lens holder 17 further includes a second internal shoulder 23 for holding a sapphire window 14 in substantially planar arrangement over an output surface 4 of the optic lens 3. The bottom opening 21 of the lens holder 17 permits any wiring or power sources to be operatively connected to the LED 2.

In this embodiment, the optical lens 3 is formed of a single piece of transparent material that allows the passage of the light emitted by the LED 2 therethrough. For example, the lens 3 may be formed of glass, plastic, or sapphire. The lens 3 includes a proximal (or light-receiving) section 9 having an input surface 10 for receiving light from the 2, and a distal for light-outputting) section 6 having a substantially flat output surface 4. The optical lens 3 also includes a collar 8 that can be seated on the internal shoulder 22 for being held within the lens holder 17, The input surface 10 includes a peripheral curved surface 12 and a central convex surface 13 that collectively form a cavity 11. The optical lens 3 includes a peripheral elliptical surface that reflects the light incident thereon via total internal reflection.

The window ring 18 includes a cylindrical internal channel 24 with a top opening 25 and a bottom opening 26. The window ring 18 contacts a top surface 15 of the sapphire window 14 to secure the sapphire window against the internal shoulder 23. In this embodiment, the bottom surface of the window ring 18 and the top surface of the lens holder 17 are threaded for releasable attachment to one another.

The external housing 5 protects the LED 2, the elliptical optic lens 3, and the sapphire window 14 from the external environment. The resilient external housing 5 permits the module 1 to be attached to the illumination device without fear of misaligning or damaging the internal LED 2, the elliptical optic lens 3, and the sapphire window 14. In some embodiments, the lens holder 17 and the window ring 18 may be formed of metals, alloys, or plastics.

In some embodiments, the module 1 may be attached to a source of power for supplying electrical power to the LED 2 and any circuitry to provide the correct voltage to the LED 2, both of which are well known in the art. By way of example, the source of power can be one or more batteries, or AC line power.

Those having ordinary skill in the art will appreciate that various changes can be made to the above embodiments without departing from the scope of the invention. Further, the elements disclosed in connection with one embodiment can be employed in other embodiments.

What is claimed is:

1. A handheld lighting system, comprising:
  a handheld housing extending from a proximal end to a distal end,
  a light module disposed removably and replaceably in said housing and having at least a light source for generating light, said light module having an adapter disposed at said distal end of the housing for coupling the light module to a light guide such that the light guide receives the light generated by the light module,
  a power module disposed within said housing and electrically coupled to said light module for providing electrical power thereto
  wherein said light module comprises:
    a hollow chamber extending from a proximal end to a distal end,
    a lens positioned in said hollow chamber, said lens having a lens body comprising an input surface for receiving light from the light source and an output surface through which light exits the lens, said lens further comprising a collar encircling at least partially said lens body,
    at least one sleeve disposed in said hollow chamber in contact with said collar for providing mechanical support to said lens,
    an optical window disposed in said hollow chamber and optically coupled to said output surface of the lens such that the light exiting the lens passes through the window before exiting the light module, and
  wherein the light source is coupled to said hollow chamber at said distal end for providing light to said input surface of the lens, and
  wherein said lens comprises:
    the lens body comprising a proximal section having said input surface and a distal section having said output surface,
  wherein said proximal section further comprises:
    a substantially elliptical peripheral surface receiving at least a portion of the light entering the lens body via said input surface and directing at least some of said received light via total internal reflection to said distal section such that at least a portion of the light directed to the distal section exits the lens body through said output surface.

2. The handheld lighting system of claim 1, wherein said adapter is removable and replaceable.

3. The handheld lighting system of claim 1, wherein said handheld housing comprises a corrugated external surface for facilitating transfer of heat generated by at least one of the light module and the power module to an external environment.

4. The handheld lighting system of claim 1, wherein said power module allows adjusting an intensity of the light generated by said light module.

5. The handheld lighting system of claim 1, wherein said light guide comprises an optical fiber.

6. The handheld lighting system of claim 1, wherein said light module comprises a pair of electrical connectors protruding through an internal wall of said housing for electrically connecting the light module to said power module.

7. The handheld lighting system of claim 6, wherein said housing comprises a first enclosure extending from said internal wall to said distal end for receiving said light module.

8. The handheld lighting system of claim 7, wherein said housing further comprises a second enclosure extending from said internal wall to said proximal end for receiving said power module.

9. The handheld lighting system of claim 1, wherein said power module comprises a rotatable outer shell, wherein a rotation of the shell results in adjusting an intensity of the light generated by said light module.

10. The handheld lighting system of claim 9, wherein said housing comprises a retaining groove for engaging with an end of said outer shell for locking said power module to said housing.

11. The handheld lighting system of claim 9, wherein said power module comprises an adjustable potentiometer electrically coupled to said light source and mechanically coupled to said rotatable shell such that a rotation of the shell results in a change of resistance of said potentiometer, thereby adjusting the intensity of the light generated by the light module.

12. The handheld lighting system of claim 1, wherein said housing comprises a thermally conductive material.

13. The handheld lighting system of claim 11, wherein said housing comprises aluminum.

14. The handheld lighting system of claim 1, wherein said light source comprises a light emitting diode (LED).

15. The handheld lighting system of claim 1, wherein said window comprises any of a sapphire window, a quartz window and a glass window.

16. The handheld lighting system of claim 15, further comprising a plurality of external threads disposed at said distal end of the hollow chamber.

17. The handheld lighting system of claim 16, further comprising a retaining window adapted for releasably coupling to said distal end of the hollow chamber.

18. The handheld lighting system of claim 17, wherein said retaining window comprises a plurality of internal threads adapted for engagement with said external threads at the distal end of the hollow chamber.

19. The handheld lighting system of claim 18, wherein said retaining window includes an opening for coupling to the adapter for coupling to the light module to the light guide.

20. The handheld lighting system of claim 19, further comprising a washer disposed between said optical window and said retaining window.

21. The handheld lighting system of claim 20, further comprising a printed circuit board on which the LED is disposed.

22. The handheld lighting system of claim 21, wherein said board comprises a plurality of electrical leads for applying electrical power from said power module to said LED.

23. The handheld lighting system of claim 22, further comprising a plate coupled to said distal end of the hollow chamber, said plate having a plurality of openings through which said electrical leads extend for coupling to said power module.

24. The handheld lighting system of claim 23, wherein said at least one sleeve comprises a pair of sleeves disposed on opposite sides of said collar.

25. The handheld lighting system of claim 1, wherein said peripheral elliptical surface is characterized by a proximal focal point and a distal focal point and is shaped such that said distal focal point is positioned in said distal section of the lens body.

26. The handheld lighting system of claim 25, wherein said distal focal point is positioned at a distance below said output surface such the light received at said distal focal point via reflection at the elliptical surface diverges towards said output surface within a solid angle subtended by said output surface.

27. The handheld lighting system of claim 26, wherein said proximal focal point of said elliptical surface is positioned substantially at said light source such that the elliptical surface transfers at least a portion of light emitted by said light source from said proximal focal point to said distal focal point.

28. The handheld lighting system of claim 27, wherein said input surface comprises a central convex portion and a peripheral portion surrounding said central convex portion.

29. The handheld lighting system of claim 28, wherein said input surface forms a surface of a cavity configured to receive at least partially the light source.

30. The handheld lighting system of claim 29, wherein said proximal focal point of the elliptical surface is disposed within said cavity.

31. The handheld lighting system of claim 30, wherein said peripheral portion of the input surface is shaped such at least a portion of the light entering the lens body via said peripheral portion propagates to said peripheral elliptical surface to be reflected thereby.

32. The handheld lighting system of claim 31, wherein said peripheral portion of the input surface is shaped such that at least about 80% of the light entering the lens body via said peripheral portion propagates to said peripheral surface of the lens body.

33. The handheld lighting system of claim 32, wherein said convex portion is characterized by a positive optical power in a range of about 50 to about 300 D.

34. The handheld lighting system of claim 33, wherein at least a portion of the light entering the lens body via said convex portion propagates to said output surface.

35. The handheld lighting system of claim 34, wherein said convex portion is configured such that the light entering said lens body via the convex portion propagates to said output surface without striking said peripheral surface.

36. The handheld lighting system of claim 35, wherein said peripheral portion of the input surface comprises a proximal concave segment and distal convex segment.

37. The handheld lighting system of claim 36, wherein said input surface is configured to capture at least about 80% of the light emitted by said light source.

38. The handheld lighting system of claim 37, wherein said input surface is configured to capture at least about 90% of the light emitted by said light source.

39. The handheld lighting system of claim 38, wherein said proximal section and said distal section are disposed about an optical axis of said lens body.

40. The handheld lighting system of claim 39, wherein said output surface is substantially flat.

41. The handheld lighting system of claim 39, wherein said output surface is substantially orthogonal to said optical axis.

42. The handheld lighting system of claim 41, wherein said collar is disposed at a boundary between said proximal section and said distal section.

43. The handheld lighting system of claim 1, wherein said lens body comprises a polymeric material.

44. The handheld lighting system of claim 43, wherein said polymeric material is any of polycarbonate, polymethylmethacrylate (PMMA) and high density polyethylene.

45. The handheld lighting system of claim 1, wherein said power module is battery operated.

46. The handheld lighting system of claim 1, wherein said power module is powered by AC line power.

* * * * *